(12) United States Patent
Jaroch et al.

(10) Patent No.: US 6,391,887 B1
(45) Date of Patent: *May 21, 2002

(54) 3,4-DIHYDROQUINOLINE DERIVATIVES AS NITROGEN MONOXIDE SYNTHASE (NOS) INHIBITORS

(75) Inventors: Stefan Jaroch; Hartmut Rehwinkel; Peter Holscher; Detlev Sulzle; Margrit Hillmann; Gerardine Anne Burton; Fiona Mcdougall McDonald, all of Berlin (DE)

(73) Assignee: Schering Aktiengesellschaft, Berlin (DE)

( * ) Notice: Subject to any disclaimer, the term of this patent is extended or adjusted under 35 U.S.C. 154(b) by 0 days.

This patent is subject to a terminal disclaimer.

(21) Appl. No.: 09/622,259

(22) PCT Filed: Feb. 9, 1999

(86) PCT No.: PCT/DE99/00382

§ 371 (c)(1),
(2), (4) Date: Aug. 14, 2000

(87) PCT Pub. No.: WO99/41240

PCT Pub. Date: Aug. 19, 1999

(30) Foreign Application Priority Data

Feb. 12, 1998 (DE) .......................... 198 06 348

(51) Int. Cl.⁷ ................. A61K 31/473; A61K 31/4738; C07D 221/16; C07D 221/12; C07D 491/04
(52) U.S. Cl. .................. 514/290; 514/291; 514/298; 514/232.8; 544/126; 546/79; 546/80; 546/89; 546/93; 546/101
(58) Field of Search ............... 546/79, 80, 89, 546/93, 101; 544/126; 514/232.8, 290, 291, 298

(56) References Cited

FOREIGN PATENT DOCUMENTS

| WO | 95/11231 | 4/1995 |
| WO | 96/14844 | 5/1996 |
| WO | 97/16430 | 5/1997 |

OTHER PUBLICATIONS

Delgado JN and Remers WA. Wilson and Gisvold's Textbook of Organic Medicinal and Pharmaceutical Chemistry. Ninth Edition. J. B. Lippincott Company. Philadephia. (1991). pp. 30–31.*
Chemical Abstracts, vol. 117, No. 9, Aug. 31, 1992, Columbus, OH, US; Abstract No. 90201c by Kuppuswamy Nagarajan et al., "Condensed heterotricyclics: synthesis of pyrazolo(3,4,–c)quinoline derivatives."

* cited by examiner

*Primary Examiner*—Evelyn Mei Huang
(74) *Attorney, Agent, or Firm*—Millen, White, Zelano, & Branigan, P.C.

(57) ABSTRACT

The invention relates to compounds of formula (I), as defined herein. The invention also relates to the use of the inventive compounds for treatment of a disease caused by the effects of nitrogen monoxide in pathological conditions.

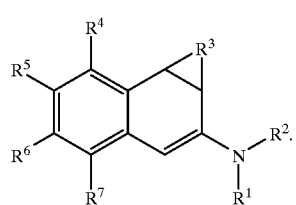

21 Claims, No Drawings

3,4-DIHYDROQUINOLINE DERIVATIVES AS NITROGEN MONOXIDE SYNTHASE (NOS) INHIBITORS

This application is the 371 of PCT/DE99/00382, filed on Feb. 9, 1999.

The invention relates to 3,4-dihydroquinoline derivatives, a process for their production and their use in pharmaceutical agents.

In human cells, there exist 3 specific forms of nitrogen monoxide synthases, which convert arginine into nitrogen monoxide (NO) and citrulline. Two constitutive NO-synthases (NOS) were thus identified that are present as $Ca^{++}$/calmodulin-dependent enzymes in the brain (ncNOS or NOS 1) or in the endothelium (ecNOS or NOS 3). The third isoform is the inducible NOS (iNOS or NOS 2), which is a $Ca^{++}$-independent enzyme and is induced after activation of different cells by endotoxin or other substances.

NOS-inhibitors and especially specific inhibitors of NOS 1, NOS 2 or NOS 3 are therefore suitable for treatment of different diseases, which are induced or aggravated by pathological concentrations of NO in cells (Clin. Neuropharmac. 18, 1995, page 482).

It has now been found that the heterocycles that are substituted according to the invention can be used especially advantageously as pharmaceutical agents.

The invention relates to the compounds of Formula I, their tautomeric and isomeric forms and their physiologically compatible salts

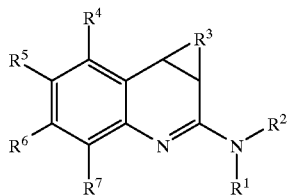

(I)

in which $R^1$ and $R^2$, independently of one another, mean:
a) Hydrogen,
b) $C_{1-6}$ alkyl,
c) $OR^8$,
d) $NR^8R^9$,
e) CN,
f) acyl,
g) $CO_2R^{10}$,
h) $CONR^8R^9$,
i) $CSNR^8R^9$, $R^3$ means:
a saturated or unsaturated $C_{1-5}$ alkylene radical, which can be substituted in 1 to 4 places with $OR^{11}$, $NR^{12}R^{13}$ or $C_{1-4}$ alkyl and in which 1 or 2 $CH_2$ groups can be replaced by O, $S(O)_n$, $NR^{14}$, =N— or carbonyl, and which can be bridged with a methano, ethano or propano group, $R^4$, $R^5$, $R^6$ and $R^7$, independently of one another, mean:
a) Hydrogen,
b) halogen,
c) $S(O)_n R^{16}$,
d) $OR^{16}{}_1$,
e) $COOR^{16}$,
f) $COR^{16}$,
g) $CONR^6R^{17}$,
h) $CSNR^{16}R^{17}$,
i) $C(NR^{18})NR^{16}R^{17}$,
j) $NR^{16}R^{19}$,
k) $C_{1-6}$ alkyl, which optionally is substituted with halogen, $OR^{16}$, $SR^{16}$, $COOR^{16}$, phenyl, 5- to 6-membered heteroaryl with 1–4 N, S or O atoms or $C_{3-7}$ cycloalkyl,
l) $C_{3-7}$ cycloalkyl,
m) $C_{2-6}$ alkenyl, optionally substituted with phenyl or halogen,
n) $C_{2-6}$ alkinyl, optionally substituted with phenyl or halogen,
o) $C_{6-10}$ aryl, which optionally is substituted with halogen, CN, $C_{1-4}$ alkyl, $SR^{16}$ or $OR^{16}$,
p) 5- to 6-membered hetaryl with 1 to 4 N, O or S atoms, which contain a slightly condensed benzene ring and can be substituted with halogen, $NO_2$, cyano, —$OR^{16}$, $SR^{16}$, $C_{1-4}$ alkyl, $CF_3$ or $NR^{16}R^{17}$,
q) CN,
r) $NO_2$,
s) $CF_3$,
t) $OCF_3$, $R^8$, $R^9$, $R^{10}$, $R^{11}$, $R^{16}$, $R^{18}$, $R^{21}$ and $R^{22}$, independently of one another, mean:
a) Hydrogen,
b) $C_{1-6}$ alkyl,
c) $C_{6-10}$ aryl, which optionally is substituted with halogen or $C_{1-4}$ alkyl, $R^{20}$ means
a) $C_{1-6}$ alkyl,
b) $C_{6-10}$ aryl, which optionally is substituted with halogen or $C_{1-4}$ alkyl, $R^{12}$, $R^{13}$, $R^{14}$ and $R^{19}$, independently of one another, mean:
a) Hydrogen,
b) $C_{1-6}$ alkyl,
b) $COR^{20}$,
c) $CO_2R^{21}$,
d) $CONR^{21}R^{22}$,
e) $CSNR^{21}R^{22}$, $R^{17}$ means
a) hydrogen,
b) $C_{1-6}$ alkyl, optionally substituted with halogens, and amino, hydroxy or sulfhydryl groups,
c) $C_{6-10}$ aryl, n means 0, 1, 2 and $R^{16}$, $R^{19}$ together with the nitrogen atom form a saturated 5-, 6- or 7-membered ring, which can contain another nitrogen, oxygen, or sulfur atom and can be substituted with $C_{1-4}$ alkyl or a phenyl, benzyl or benzoyl radical that is optionally substituted with halogen.

The compounds of the formula can be present as tautomers, stereoisomers or geometric isomers. The invention also comprises all possible isomers, such as E- and Z-isomers, S- and R-enantiomers, cis- and trans-diastereomers, racemates and mixtures thereof, including the tautomeric compounds of Formulas Ia and Ib (for $R^2$=hydrogen).

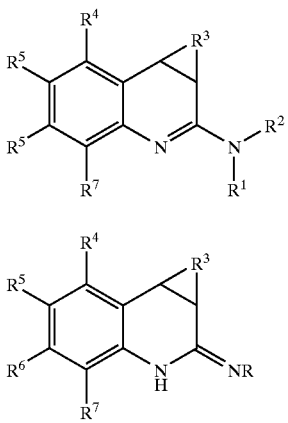

The physiologically compatible salts can be formed with inorganic and organic acids, such as, for example, oxalic acid, lactic acid, citric acid, fumaric acid, acetic acid, maleic acid, tartaric acid, phosphoric acid, hydrochloric acid, hydrobromic acid, sulfuric acid, p-toluenesulfonic acid, methanesulfonic acid, i.a.

For salt formation of acid groups, the inorganic or organic bases are also suitable, which are known for the formation of physiologically compatible salts, such as, for example, alkali hydroxides, such as sodium and potassium hydroxide, alkaline-earth hydroxides, such as calcium hydroxide, ammonia, amines such as ethanolamine, diethanolamine, triethanolamine, N-methylglucamine, tris-(hydroxymethyl)-methylamine, etc.

In each case, alkyl means a straight-chain or branched alkyl group, such as, e.g., methyl, ethyl, propyl, isopropyl, n-butyl, sec-butyl, tert-butyl, n-pentyl, sec-pentyl, tert-pentyl, neopentyl, n-hexyl, sec-hexyl, heptyl, octyl, whereby 1 to 4 carbon atoms are preferred.

If the alkyl radical is halogenated, the latter can be present in one or more places, whereby trifluoromethyl is preferred.

Alkenyl and alkinyl radicals are straight-chain or branched in each case and preferably contain up to 4 carbon atoms. For example, the following radicals can be mentioned: vinyl, 2-propenyl, 1-propenyl, 2-butenyl, 1-butenyl, 1-butenyl, 2-butenyl, 1-methyl-1-propenyl, 2-methyl-2-propenyl, 3-methyl-2-propenyl, ethinyl, 1-propinyl, 2-propinyl, 1-butinyl, 2-butinyl.

Cycloalkyl is defined respectively as cyclopropyl, cyclobutyl, cyclopentyl, cyclohexyl or cycloheptyl.

Halogen means respectively fluorine, chlorine, bromine or iodine.

Aryl is defined respectively as naphthyl or especially phenyl, which can be substituted by the same or a different component in one to three places.

The hetaryl radicals can contain a slightly condensed benzene ring and can be substituted by the same or a different component in one to three places and can be bonded via the heteroatom or a carbon atom. For example, the following 5- and 6-ring heteroaromatic compounds are suitable in each case: Imidazole, indole, isoxazole, isothiazole, furan, oxadiazole, oxazole, pyrazine, pyridazine, pyrimidine, pyridine, pyrazole, pyrrole, tetrazole, thiazole, triazole, thiophene, thiadiazole, benzimidazole, benzofuran, benzoxazole, isoquinoline, quinoline. Preferred are 5- or 6-membered heteroaromatic compounds with 1 to 2 nitrogen, oxygen or sulfur atoms and especially furanyl and thienyl. As substituents of the heteroaryl radicals, especially $NO_2$, CN, halogen, $C_{1-6}$ alkyl and $CF_3$ are suitable.

As heterocycle $NR^{16}R^{19}$, for example, piperidine, pyrrolidine, morpholine, thiomorpholine, hexahydroazepine or piperazine can be mentioned. The heterocycle can be substituted in 1 to 3 places with $C_{1-4}$ alkyl or a phenyl, benzyl or benzoyl radical that is optionally substituted with halogen. Especially suitable are 6-membered saturated heterocycles that can contain another heteroatom and that can be substituted in 1 or 2 places. For example, there can be mentioned: N-methyl-piperazine, 2,6-dimethylmorpholine, phenylpiperazine or 4-(4-fluorobenzoyl)-piperidine.

The acyl radical is derived from straight-chain or branched aliphatic $C_{1-6}$ carboxylic acids, such as, for example, formic acid, acetic acid, propionic acid, butyric acid, trimethylacetic acid or caproic acid or from known benzenesulfonic acids, which can be substituted with halogen or $C_{1-4}$ alkyl, and $C_{1-4}$ alkanesulfonic acids, such as, for example, methanesulfonic acid, and p-toluenesulfonic acid. Preferably alkanoyls can be mentioned.

As preferred meanings of $R^1$ and $R^2$, hydrogen, $C_{1-6}$ alkyl and hydroxy can be mentioned.

$R^3$ preferably means alkylene with 1 to 5 carbon atoms, in which a $CH_2$ group can be replaced by oxygen or sulfur. For example, $—CH_2—O—CH_2—$, $—CH_2—S—CH_2—$, $—(CH_2)_3—$, $—(CH_2)_4—$ and $—(CH_2)_5—$ can be mentioned.

Preferred embodiments for $R^4$, $R^5$, $R^6$ and $R^7$ are:
a) Hydrogen,
b) halogen,
c) $SR^{16}$,
d) $OR^{16}$,
e) $COOR^{16}$,
f) $COR^{16}$,
g) $CONR^{16}R^{17}$,
h) $NR^{16}R^{19}$,
i) $C_{1-6}$ alkyl, which optionally is substituted with halogen, $COOR^{16}$ or phenyl,
j) $C_{2-6}$ alkenyl, optionally substituted with phenyl or halogen,
k) $C_{2-6}$ alkinyl, optionally substituted with phenyl or halogen,
l) phenyl, which optionally is substituted with halogen, CN, $C_{1-4}$ alkyl, $SR^{16}$ or $R^{16}$,
m) 5- to 6-membered heteroaryl with 1 to 4 N, O or S atoms, which with halogen, $NO_2$, cyano, $C_{1-4}$ alkyl or $CF_3$,
n) CN,
o) $NO_2$,
p) $CF_3$,
q) $OCF_3$.

Preferred meanings of $R^{12}$, $R^{13}$, $R^{14}$, $R^{17}$ and $R^{19}$ are hydrogen and $C_{1-6}$ alkyl. In particular 1–2 substituents $R^4$, $R^5$, $R^6$ or $R^7$ are present, which do not mean hydrogen.

The invention also relates to the use of the compounds according to the invention for the production of a pharmaceutical agent for treating and preventing diseases, which are caused by the action of nitrogen monoxide at pathological concentrations. These include neurodegenerative diseases, inflammatory diseases, auto-immune diseases, and cardiovascular diseases.

For example, there can be mentioned: cerebral ischemia, hypoxia and other neurodegenerative diseases, which are brought into contact with inflammations, such as multiple sclerosis, amyotrophic lateral sclerosis and comparable sclerotic diseases, Parkinson's Disease, Huntington's Disease, Korksakoff's Disease, epilepsy, vomiting, sleep disorders, schizophrenia, depression, migraine, hypoglycemia, dementia, such as, e.g., Alzheimer's Disease, HIV-dementia and presenile dementia.

They are also suitable for treating diseases of the cardiovascular system and for treating auto-immune and/or inflammatory diseases, such as hypotension, ARDS (adult respiratory distress syndrome), sepsis or septic shock, rheumatoid arthritis, osteoarthritis, insulin-dependent diabetes mellitus (IDDM), inflammatory disease of the pelvis/intestine (bowel disease), meningitis, glomerulonephritis, acute and chronic liver diseases, diseases by rejection (for example allogenic heart, kidney or liver transplants) or inflammatory skin diseases such as psoriasis, etc. Based on their profile of action, the compounds according to the invention are very well suited for inhibiting the neuronal NOS.

To use the compounds according to the invention as pharmaceutical agents, they are brought into the form of a pharmaceutical preparation, which in addition to the active ingredient contains vehicles, adjuvants and/or additives that are suitable for enteral or parenteral administration. The administration can be done orally or sublingually as a solid in the form of capsules or tablets or as a liquid in the form of solutions, suspensions, elixirs, aerosols or emulsions or rectally in the form of suppositories or in the form of injection solutions that can also optionally be used subcutaneously, intramuscularly or intravenously, or topically or intrathecally. As adjuvants for the desired pharmaceutical agent formulation, the inert organic and inorganic support media that are known to one skilled in the art are suitable, such as, e.g., water, gelatin, gum arabic, lactose, starch, magnesium stearate, talc, vegetable oils, polyalkylene glycols, etc. Moreover, preservatives, stabilizers, wetting agents, emulsifiers or salts for changing the osmotic pressure or buffers can optionally be contained.

For parenteral administration, especially injection solutions or suspensions, especially aqueous solutions of the active compounds in polyhydroxyethylated castor oil, are suitable.

As vehicle systems, surface-active adjuvants such as salts of bile acids or animal or plant phospholipids, but also mixtures thereof as well as liposomes or their components can be used.

For oral administration, especially tablets, coated tablets or capsules with talc and/or hydrocarbon vehicles or binders, such as, for example, lactose, corn or potato starch, are suitable. The administration can also be done in liquid form, such as, for example, as a juice, to which optionally a sweetener is added.

The dosage of the active ingredients can vary depending on method of administration, age and weight of the patient, type and severity of the disease that is to be treated and similar factors. The daily dose is 1–2000 mg, preferably 20–500 mg, whereby the dose can be given as an individual dose to be administered one time or divided into 2 or more daily doses.

The NOS-inhibitory action of the compounds of Formula (I) and their physiologically compatible salts can be determined according to the methods by Bredt and Snyder in Proc. Natl. Acad. Sci. USA (1989) 86, 9030–9033. For the bNOS inhibition of Example 21 (4-amino-7-(4-morpholinyl)-2,3,3a,9b-tetrahydro-1H-cyclopenta[c]quinoline) and Example 22 (4-amino-7-(methoxycarbonylethyl)-2,3,3a,9b-tetrahydro-1H-cyclopenta[c]quinoline), $IC_{50}=1.4$ μm and 1.1 μm.

The production of the compounds according to the invention is carried out in that a compound of formula (II) or its salt

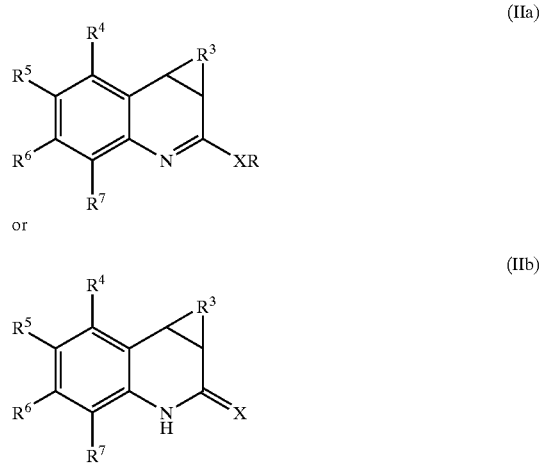

in which $R^3$ to $R^7$ has the above meaning, R is methyl or ethyl and X is oxygen or sulfur, is reacted with ammonia, primary or secondary amines, hydroxylamine and its derivatives or hydrazine and its derivatives, and optionally then the isomers are separated or the salts are formed.

The reaction with ammonia is possible under pressure in autoclaves with excess ammonia at low temperatures (−78° C.) or by stirring in methanol that is saturated with ammonia. Thiolactams are preferably reacted. If the reaction is carried out with amines, first the iminoethers or iminothioethers are produced from lactam or thiolactam as intermediate compounds (e.g., with methyl iodide or dimethyl sulfate), and the latter are reacted with or without isolation with the corresponding amines or their salts.

The isomer mixtures can be separated into enantiomers or E/Z-isomers according to commonly used methods, such as, for example, crystallization, chromatography or salt formation. The enantiomers can also be obtained by chromatography on chiral phases as well as by stereoselective syntheses.

The production of the salts is carried out in the usual way, by a solution of the compound of Formula (I) being mixed with the equivalent amount of acid or excess acid, which optionally is in solution, and the precipitate being separated or the solution being worked up in the usual way.

If the production of the starting compounds is not described, the latter are known and commercially available or can be produced analogously to known compounds or according to processes that are described here.

Thiolactams of Formula (IIb, X=S) are obtained, for example, from lactams with phosphorus pentasulfide ($P_4S_{10}$) or 2,4-bis(4-methoxyphenyl)-1,3,2,4-dithiaphosphetane-2,4-disulfide (Lawesson's reagent) in suitable solvents. Compounds of Formula (IIa) can be obtained by, for example, reaction with Meerwein reagent (trimethyloxonium tetrafluoroborate).

The production of the compounds of Formula (IIb, X=O) is done in the way that is known to one skilled in the art. It can be done, for example, in that a compound of Formula (III)

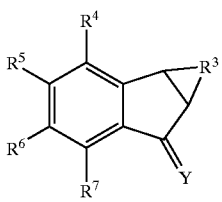

(III)

in which $R^3$ to $R^7$ have the above meaning and Y=O, after conversion into the oxime (Y=NOH), for example with a hydroxylammonium salt and sodium acetate, is subjected to a Beckmann epoxidation (R. E. Gawley, Org. Reactions 1988, 35, 1), for example in polyphosphoric acid (cf. K. Hino, Y. Nagai, H. Uno, Chem. Pharm. Bull. 1988, 36, 2386).

Another synthesis method starts from a compound of Formula (IV),

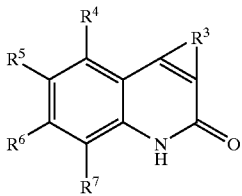

(IV)

which is reduced to lactam (II) with an alkali or alkaline-earth metal or an amalgam thereof in alcohol (cf. B. K. Blount, W. H. Perkin, S. G. P. Plant, J. Chem. Soc. 1929, 1975, R. Brettle, S. M. Shibib, J. Chem. Soc. Perkin Trans. 1, 1981, 2912).

The production of indanones of type (III) is carried out in the way that is known to one skilled in the art, e.g., according to W. Baker, P. G. Jones, J. Chem. Soc. 1951, 787, S. Ohta, M. Yamashita, K. Arita, T. Kajiura, I. Kawasaki, K. Noda, M. Izumi, Chem. Pharm. Bull. 1995, 43, 1294; C. Santelli-Rouvier, M. Santelli, Synthesis 1983, 429.

The production of quinolones of type (IV) is carried out in the way that is known to one skilled in the art, e.g., according to B. K. Blount, W. H. Perkin, S. G. P. Plant, J. Chem. Soc. 1929, 1975; W. Ried, W. Käppeler, Liebigs Ann. Chem. 1965, 688, 177; L. A. White, R. C. Storr, Tetrahedron 1996, 52, 3117.

The production of the compound of Formula (III) can be carried out, for example, in that an aromatic compound (V) is reacted with an activated acid derivative, such as, for example, an acid chloride (Z=Cl) or anhydride (Z=OCOR) in the presence of a Lewis acid, such as, for example, $AlCl_3$, $SnCl_4$, $ZnCl_2$, $SbCl_5$, $FeCl_3$, $BF_3$-etherate, in an inert solvent, such as, for example, dichloromethane, dichloroethane or benzene at 0° C. up to boiling temperature of the corresponding solvent (see, e.g., W. Baker, P. G. Jones, J. Chem. Soc. 1951, 787). As an alternative, the ketones of Formula (VII) that are produced according to methods that are known to one skilled in the art (e.g., according to S. Ohta, M. Yamashita, K. Arita, T. Kajiura, I. Kawasaki, K. Noda, M. Izumi, Chem. Pharm. Bull. 1995, 43, 1294) can be cyclized with Bronstedt acids, such as, for example, sulfuric acid, p-toluenesulfonic acid, methanesulfonic acid, phosphoric acid or polyphosphoric acid (cf. C. Santelli-Rouvier, M. Santelli, Synthesis 1983, 429).

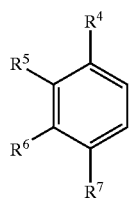

(V)

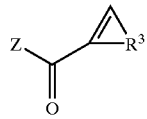

(VI)

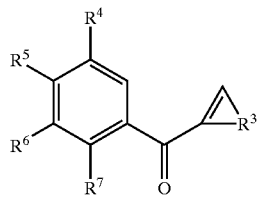

(VII)

The production of the compound of Formula (IV) can be carried out, for example, in that a beta-ketoamide of Formula (VIII) or its derivative is treated with an acid, for example, sulfuric acid, phosphoric acid, polyphosphoric acid or trifluoroacetic acid or methanesulfonic acid (e.g., B. K. Blount, W. H. Perkin, S. G. P. Plant, J. Chem. Soc. 1929, 1975; W. Ried, W. Käppeler, Liebigs Ann. Chem. 1965, 688, 177).

(VIII)

The introduction of substituents $R^4$–$R^7$ can be carried out at the stage of compounds (III) and (IV).

In the precursor stages, optionally sulfides are oxidized, esters are saponified, acids are esterified, hydroxy groups are etherified or acylated, amines are acylated, alkylated, diazotized, halogenated, $NO_2$ is introduced or reduced, reacted with isocyanates or isothiocyanates, the isomers are separated or the salts are formed.

The saponification of an ester group can be done in a basic or acidic manner by hydrolysis being performed at room temperature or at a higher temperature up to boiling temperature of the reaction mixture in the presence of alkali hydroxides in ethanol or other alcohols or using acids such as, e.g., hydrochloric acid, and optionally salts of 3,4-cycloalkanodihydroquinolines are further processed.

The esterification of carboxylic acid is carried out in a way that is known in the art with diazomethane or the corresponding alcohol in acid or in the presence of an activated acid derivative. As activated acid derivatives, for example, acid chloride, acid imidazolide or acid anhydride are suitable.

In addition, a nitro group or halogen, especially bromine, can be introduced by electrophilic aromatic substitution. Mixtures that are produced in this case can be separated in the usual way, even using HPLC.

If a nitrile is present, the latter can be saponified according to known processes or can be introduced into the corresponding amine, tetrazole or amidoxime.

The Friedel-Crafts acylation is used successfully in lactams of type (IIb, X=O); then the lactam can be converted selectively into the thiolactam.

The introduction of an $NO_2$ group is possible by a number of known nitration methods. For example, nitration can be performed with nitrates or with nitronium tetrafluoroborate in inert solvents, such as halogenated hydrocarbons or in sulfolane or glacial acetic acid. Introduction by, e.g., nitrating acid in water, acetic acid or concentrated sulfuric acid as a solvent is also possible at temperatures of between –10° C. and 30° C.

The reduction of the nitro group or optionally the cyano group to the amino group is carried out catalytically in polar solvents at room temperature or at an elevated temperature under hydrogen pressure. As catalysts, metals such as Raney nickel or noble metal catalysts such as palladium or platinum optionally in the presence of barium sulfate or on vehicles are suitable. Instead of hydrogen, ammonium formate or formic acid can also be used in a known way. Reducing agents such as tin(II) chloride or titanium(III) chloride can also be used, such as complex metal hydrides, optionally in the presence of heavy metal salts. For nitro groups, reduction with zinc in water-ethanol-THF/ammonium chloride or iron in acetic acid has proven its value.

If a single or multiple alkylation of an amino group or a CH-acid carbon position is desired, alkylation can be performed with, for example, alkyl halides according to commonly used methods. Protection of the lactam group as an anion by a second equivalent base or by a suitable protective group optionally is necessary.

The acylation of the amino group is carried out in the usual way with, for example, an acid halide or acid anhydride, optionally in the presence of a base.

The introduction of the halogens chlorine, bromine or iodine via the amino group can also be carried out, for example, according to Sandmeyer, by the diazonium salts that are formed intermediately with nitrites being reacted with Cu(I) chloride or Cu(I) bromide in the presence of the corresponding acids such as hydrochloric acid or hydrobromic acid or being reacted with potassium iodide.

New compounds were identified by one or more of the following methods: melting point, mass spectroscopy, infrared spectroscopy, nuclear magnetic resonance spectroscopy (NMR). NMR spectra were measured with a Bruker 400 MHz device; the (deuterated) solvents are respectively indicated and abbreviated as follows: $CDCl_3$ (chloroform), $CD_3OD$ ($[D_4]$-methanol), DMSO ($[D_6]$-dimethyl sulfoxide). Alterations are indicated in delta and ppm. Here: m means multiplet, several signals; s means singlet; d means doublet; dd means double doublet, etc.; t means triplet; q means quartet; H means hydrogen protons. In addition, THF means tetrahydrofuran, DMF means N,N-dimethylformamide, MeOH means methanol, and ml means milliliter. All solvents are p.A. grade, unless otherwise indicated. All reactions are performed under protective gas, unless these are aqueous solutions. Melting points are indicated in degrees Celsius and are not corrected.

Below, the production of precursors, intermediate products and products is described by way of example.

Starting Compounds

A) 1,2,3,3a,5,9b-Hexahydrocyclopenta[c]quinolin-4-one
According to Method A
2,3,3a,8a-Tetrahydro-1H-cyclopent[a]inden-8-one (1.06 g, 6.0 mmol) (W. Baker, P. G. Jones, J. Chem. Soc. 1951, 787) is dissolved with hydroxylammonium sulfate (1.96 g, 12.0 mmol) and sodium acetate (24.0 mmol, 3.28 g) in THF-ethanol-water 1:1:1 (120 ml) and stirred for five days at room temperature. The reaction mixture is concentrated by evaporation and diluted with ethyl acetate (150 ml), washed with saturated NaCl (50 ml), dried ($Na_2SO_4$) and concentrated by evaporation in a vacuum. The residue is purified by column chromatography ($SiO_2$) with the eluant hexane-ethyl acetate. Yield: 0.88 g (78%), melting point 118–20° C.; the thus obtained oxime (0.65 g, 3.5 mmol) is added to 120° C. phosphoric acid (10 ml). The batch is stirred for 30 minutes at 120° C. After cooling, it is taken up in water (150 ml), and the aqueous solution is extracted with ethyl acetate (3×150 ml). The combined ethyl acetate extracts are dried ($Na_2SO_4$) and concentrated by evaporation in a vacuum. The residue is purified by column chromatography ($SiO_2$) with the eluant hexane-ethyl acetate.

Yield: 202 mg (31%), melting point 133–5° C.
According to Method B
1,2,3,5-Tetrahydrocyclopenta[c]quinolin-4-one (410 mg, 2.21 mmol) (W. Ried, W. Käppeler, Liebigs Ann. Chem. 1965, 688, 177) is dissolved in methanol (25 ml) and mixed with magnesium (538 mg, 22.1 mmol). After 3 hours of stirring at room temperature, the batch is filtered, the filter residue is washed with ethyl acetate, and the combined filtrates are concentrated by evaporation. Purification by column chromatography ($SiO_2$) with the eluant hexane-ethyl acetate yields 290 mg (71%) of the product.

$^1$H-NMR ($CDCl_3$): δ=1.60–1.80 (m, 3H), 2.03–2.20 (m, 2H), 2.26–2.40 (m, 1H), 2.96 (td, 1H), 3.20–3.32 (m, 1H), 6.78 (dd, H), 7.00 (td, 1H), 7.17 (td, 1H), 7.21 (dd, 1H), 8.32 (br. s, 1H).

MS (EI) m/e=187 ($M^+$)

Produced by synthesis according to method A are:

6a,7,8,9,10,10a-Hexahydro-5H-phenanthridin-6-one 1,2,3,4,4a,9a-Hexahydrofluoren-9-oxime (3.18 g) is obtained from 1,2,3,4,4a,9a-hexahydrofluoren-9-one (2.7 g, 14.5 mmol). 2.0 g of it is converted with polyphosphoric acid (20 ml) into 0.22 g (11%) of product.

Melting point 212–3° C. (column chromatography on silica gel, eluant: ethyl acetate-hexane)

$^1$H-NMR ($CDCl_3$): 1.40–1.85 (m, 7H), 2.38 (m, 1H), 2.85 (m, 1H), 2.98 (m, 1H), 6.77 (dd, 1H), 7.03 (td, 1H), 7.19 (dd, 1H), 7.21 (td, 1H), 8.04 (br. s, 1H).

MS (EI) m/e=201 ($M^+$)

1,2,3,4,4a,10b-Hexahydro-5H-phenanthridin-6-one accumulates as a more polar by-product.

1,2,3,4,5,5a,7,11b-Octahydrocyclohepta[c]quinolin-6-one 5,6,7,8,9,9a-Hexahydro-4bH-benz[a]azulen-10-oxime (2.9 g) is obtained from 5,6,7,8,9,9a-hexahydro-4bH-benz[a]azulen-10-one (2.89 g). 0.33 g of product is produced from it with polyphosphoric acid (20 ml).

$^1$H-NMR ($CDCl_3$): 1.40–1.90 (m, 9H), 2.12 (m, 1H), 2.88 (m, 1H), 3.09 (m, 1H), 6.75 (dd, 1H), 7.01 (td, 1H), 7.16 (td, 1H), 7.18 (dd, 1H), 8.05 (br. s, 1H).

MS (EI) m/e=215 ($M^+$)

1,2,3,4,5,5a,7,11b-Octahydrocyclohepta[c]isoquinolin-7-one accumulates as a more polar by-product.

B) 1,2,3,3a,5,9b-Hexahydrocyclopenta[c]quinoline-4-thione
1,2,3,3a,5,9b-Hexahydrocyclopenta[c]quinolin-4-one (153 mg, 0.82 mmol) and Lawesson's reagent (363 mg, 0.9 mmol) are stirred in dimethoxyethane (20 ml) at room temperature. After 3 hours, another portion of Lawesson's reagent (363 mg, 0.9 mmol) is added to it. After 3 hours, the batch is concentrated by evaporation, and the residue is purified by column chromatography on silica gel (eluant: hexane-ethyl acetate).

Yield: 140 mg (84%), melting point 138–40° C.

$^1$H-NMR (CDCl$_3$): 1.60–1.80 (m, 2H), 1.93 (m, 1H), 2.10–2.40 (m, 3H), 3.32 (m, 2H), 6.86 (dd, 1H), 7.12 (td, 1H), 7.20 (td, 1H), 7.25 (dd, 1H), 9.87 (br. s, 1H).

MS (EI) m/e=203 (M$^+$)

Produced analogously by synthesis are:

6a,7,8,9,10,10a-Hexahydro-5H-phenanthridine-6-thione 26 mg (54%) of product is obtained from 6a,7,8,9,10,10a-hexahydro-5H-phenanthridin-6-one (44 mg, 0.22 mmol).

$^1$H-NMR (CDCl$_3$): 1.45–1.82 (m, 6H), 1.99 (m, 2H), 3.05–3.20 (m, 2H), 6.85 (dd, 1H), 7.13 (td, 1H), 7.16 (td, 1H), 7.23 (dd, 1H), 9.73 (br. s, 1H).

1,2,3,4,5,5a,7,11b-Octahydrocyclohepta[c]quinoline-6-thione 100 mg (94%) of product is obtained from 1,2,3,4,5,5a,7,11b-octahydrocyclohepta[c]quinolin-6-one (100 mg, 0.46 mmol).

Melting point 112° C.

$^1$H-NMR (CDCl$_3$): 1.40–2.10 (m, 10H), 3.13–3.29 (m, 2H), 6.85 (dd, 1H), 7.10–7.25 (m, 3H), 9.76 (br. s, 1H).

MS (EI) m/e=231 (M$^+$)

EXAMPLE 1

4-Amino-2,3,3a,9b-tetrahydro-1H-cyclopenta[c]quinoline 1,2,3,3a,5,9b-Hexahydrocyclopenta[c]quinoline-4-thione (110 mg, 0.54 mmol) is stirred in 7 M methanolic ammonia solution (50 ml) for 15 hours at room temperature. The batch is concentrated by evaporation in a vacuum. The residue is purified by column chromatography on silica gel with dichloromethane-methanol-concentrated NH$_4$OH as an eluant.

Yield: 100 mg (99%)

$^1$H-NMR (CDCl$_3$): 1.41–1.98 (m, 4H), 2.11–2.25 (m, 2H), 2.83 (q, 1H), 3.30 (q, 1H), 4.44 (br., 2H), 6.96–7.05 (m, 2H), 7.12–7.29 (m, 2H).

MS (EI) m/e=186 (M$^+$)

EXAMPLE 2

6-Amino-6a,7,8,9,10,10a-hexahydrophenanthridine

Analogously to Example 1, 6a,7,8,9,10,10a-hexahydro-5H-phenanthridine-6-thione (26 mg, 0.12 mmol) is converted into 10 mg (42%) of product.

$^1$H-NMR (CDCl$_3$): 1.20–1.80 (m, 6H), 1.90–2.23 (m, 2H), 2.43–3.05 (m, 2H), 5.35 (br., 2H), 7.00 (m, 2H), 7.18 (m, 2H)

MS (EI) m/e=200 (M$^+$)

EXAMPLE 3

6-Amino-2,3,4,5,5a,11b-hexahydro-1H-cyclohepta[c]quinoline

Analogously to Example 1, 1,2,3,4,5,5a,7,11b-octahydrocyclohepta[c]quinoline-6-thione (90 mg, 0.39 mmol) is converted into 70 mg (84%) of product.

$^1$H-NMR (CD$_3$OD): 1.30–1.78 (m, 9H), 2.00 (m, 2H), 3.11 (t, 1H), 6.92 (dd, 1H), 6.96 (td, 1H), 7.07 (td, 1H), 7.17 (dd, 1H).

MS (EI) m/e=214 (M$^+$)

EXAMPLE 4

4-Amino-7-nitro-2,3,3a,9b-tetrahydro-1H-cyclopenta[c]quinoline

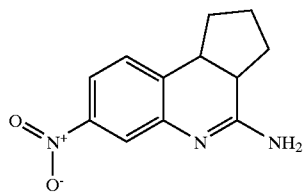

6-Nitro-2,3,3a,8a-tetrahydro-1H-cyclopent[a]inden-8-one and 5-methyl-6-nitro-2,3,3a,8a-tetrahydro-1H-cyclopent[a]inden-8-one Cyclopentene-1-carboxylic acid (3.92 g, 35 mmol) is refluxed for 30 minutes in 35 ml of thionyl chloride. The solution is concentrated by evaporation in a vacuum, and thionyl chloride radicals are azeotropically removed with toluene. The residue is taken up in benzene, mixed with aluminum trichloride (23.33 g, 175 mmol), refluxed for 1 hour and left for 1 week at room temperature. The batch is poured onto ice and extracted with ether. The organic phase is washed with water, dried (Na$_2$SO$_4$) and concentrated by evaporation in a vacuum. Column chromatography on silica gel with ether-hexane yielded 3.85 g of a 2:1 mixture of 2,3,3a,8a-tetrahydro-1H-cyclopent[a]inden-8-one* and 5-methyl-2,3,3a,8a-tetrahydro-1H-cyclopent[a]inden-8-one$^\#$. $^1$H-NMR (CDCl$_3$): δ=1.06–1.25 (m, 1H), 1.61 (m, 1H), 1.79–2.12 (m, 4H), 2.45$^\#$ (s, –3/3H), 3.03–3.12 (m, 1H), 3.72$^\#$ (t) and 3.78* (t, Σ 1H); 7.16$^\#$ (d), 7.28$^\#$ (s), 7.37* (t), 7.49* (d), 7.62$^\#$ (d), 7.62* (t) and 7.68* (d, Σ–4H). This mixture is slowly mixed at 5° C. with 20 ml of nitrating acid (prepared from 10 ml of 96% sulfuric acid and 10 ml of 65% nitric acid). After 45 minutes at 5–10° C., the batch is poured onto ice and extracted with ether. The combined ether extracts are washed with saturated NaHCO$_3$, dried (Na$_2$SO$_4$) and concentrated by evaporation in a vacuum. Column chromatography on silica gel with ether-hexane yields 3.76 g of a 2:1 mixture of 6-nitro-2,3,3a,8a-tetrahydro-1H-cyclopent[a]inden-8-one* and 5-methyl-6-nitro-2,3,3a,8a-tetrahydro-1H-cyclopent[a]inden-8-one$^\#$.

$^1$H-NMR (CDCl$_3$): δ=1.09–1.26 (m, 1H), 1.70 (m, 1H), 1.82–2.19 (m, 4H), 2.68$^\#$ (s, –3/3H), 3.16$^\#$ (ddd) and 3.22* (ddd, Σ 1H), 3.81$^\#$ (t) and 3.90* (t, Σ 1H); 7.46$^\#$ (s, 1/3H), 7.67* (dd, 2/3H), 8.23$^\#$ (s, 1/3H), 8.47* (dd, 2/3H), 8.51* (d, 2/3H).

7-Nitro-1,2,3,3a,5,9b-hexahydrocyclopenta[c]quinolin-4-one 8-Methyl-7-nitro-1,2,3,3a,5,9b-hexahydrocyclopenta[c]quinolin-4-one The mixture that consists of 6-nitro-2,3,3a,8a-tetrahydro-1H-cyclopentta]inden-8-one and 5-methyl-6-nitro-2,3,3a,8a-tetrahydro-1H-cyclopent[a]inden-8-one (3.76 g) is dissolved with hydroxylammonium sulfate (5.58 g, 34 mmol) and sodium acetate (9.25 g, 68 mmol) in THF-ethanol-water 1:1:1 (180 ml). The batch is stirred for 6 hours at 60° C., left for three days at room temperature, concentrated by evaporation, diluted with ether, washed with saturated NaCl, dried (Na$_2$SO$_4$) and concentrated by evaporation in a vacuum. The residue is purified on silica gel with the eluant ether-hexane. Yield: 3.76 g; the oxime mixture is dissolved at 120° C. in polyphosphoric acid. The batch is stirred for four hours at 120° C., it is poured onto ice water after cooling and extracted with ethyl acetate. The combined extracts are dried (Na$_2$SO$_4$) and concentrated by evaporation in a vacuum. The residue is prepurified on silica gel with ethyl acetate-hexane, and the mixture is then separated using preparative HPLC (LC.50 Novapak column, eluant: methanol-aqueous ammonium acetate solution):

91 mg of 7-nitro-1,2,3,3a,5,9b-hexahydrocyclopenta[c] quinolin-4-one:

$^1$H-NMR (CDCl$_3$): δ=1.57–1.86 (m, 3H), 2.10–2.25 (m, 2H), 2.41 (m, 1H), 3.03 (td, 1H), 3.36 (q, 1H), 7.38 (d, 1H), 7.66 (d, 1H), 7.88 (dd, 1H), 8.58 (br. s, 1H);

60 mg of 8-methyl-7-nitro-1,2,3,3a,5,9b-hexahydrocyclopenta[c]quinolin-4-one:

$^1$H-NMR (CDCl$_3$): δ=1.49–1.81 (m, 3H), 2.09–2.22 (m, 2H), 2.38 (m, 1H), 2.56 (s, 3H), 2.98 (td, 1H), 3.29 (q, 1H), 7.16 (s, 1H), 7.45 (s, 1H), 8.40 (br. s, 1H)

7-Nitro-1,2,3,3a,5,9b-hexahydrocyclopenta[c] quinoline-4-thione

7-Nitro-1,2,3,3a,5,9b-hexahydrocyclopenta[c]quinolin-4-one (91 mg, 0.30 mmol) is stirred with Lawesson's reagent (170 mg, 0.43 mmol) for 6 hours at room temperature. The batch is concentrated by evaporation in a vacuum, and the residue is purified on silica gel with toluene: 52 mg (54%) of product.

$^1$H-NMR ([D$_6$]-DMSO): δ=1.47–1.77 (m, 3H), 2.09–2.24 (m, 3H), 3.40 (m, 2H), 7.57 (d, 1H), 7.91 (dd, 1H), 8.00 (d, 1H), 12.40 (br. s, 1H).

4-Amino-7-nitro-2,3,3a,9b-tetrahydro-1H-cyclopenta[c]quinoline

7-Nitro-1,2,3,3a,5,9b-hexahydrocyclopenta[c]quinoline-4-thione (47 mg, 0.19 mmol) is stirred in 7N methanolic ammonia (10 ml) for 15 hours at room temperature. The batch is concentrated by evaporation in a vacuum. The residue is purified on silica gel with dichloromethane-2-propanol/methanol: 21 mg (48%) of product.

$^1$H-NMR ([D$_6$]-DMSO): δ=1.45–1.66 (m, 3H), 1.87 (m, 1H), 2.06–2.22 (m, 2H), 2.77 (m, 1H), 3.33 (m, 1H), 7.06 (br., 2H), 7.37 (d, 1H), 7.52 (s, 1H), 7.67 (d, 1H);

MS (EI) m/e=231 (M$^+$).

EXAMPLE 5

4-Amino-8-methyl-7-nitro-2,3,3a,9b-tetrahydro-1H-cyclopenta[c]quinoline

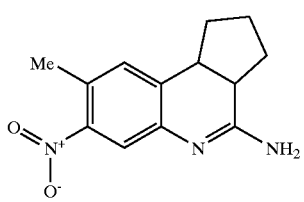

8-Methyl-7-nitro-1,2,3,3a,5,9b-hexahydrocyclopenta[c]quinoline-4-thione

As described for Example 4, 8-methyl-7-nitro-1,2,3,3a,5,9b-hexahydrocyclopenta[c]quinolin-4-one (60 mg, 0.24 mmol) is reacted with Lawesson's reagent (105 mg, 0.26 mmol) to form 47 mg (75%) of product.

$^1$H-NMR (CDCl$_3$): δ=1.66–1.79 (m, 2H), 1.88 (m, 1H), 2.16–2.41 (m, 3H), 2.59 (s, 3H), 3.32 (m, 2H), 7.22 (s, 1H), 7.52 (s, 1H), 9.61 (br. s, 1H).

4-Amino-7-nitro-2,3,3a,9b-tetrahydro-1H-cyclopenta[c]quinoline

As described for Example 4, 8-methyl-7-nitro-1,2,3,3a,5,9b-hexahydrocyclopenta[c]quinoline-4-thione (42 mg, 0.16 mmol) is reacted with 7N methanolic ammonia solution (10 ml) to form 30 mg (77%) of product.

$^1$H-NMR (CDCl$_3$): δ=1.44–1.61 (m, 2H), 1.83–1.94 (m, 2H), 2.03–2.21 (m, 2H), 2.50 (s, 3H), 2.91 (q, 1H), 3.23 (q, 1H), 4.93 (br., 2H), 7.05 (s, 1H), 8.06 (s, 1H);

MS (EI) m/e=245 (M$^+$).

EXAMPLE 6

4-Amino-8-nitro-2,3,3a,9b-tetrahydro-1H-cyclopenta[c]quinoline

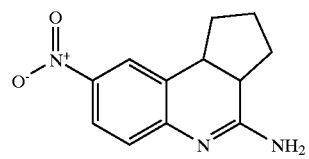

8-Nitro-1,2,3,3a,5,9b-hexahydrocyclopenta[c] quinolin-4-one

65% Nitric acid (0.33 ml) is mixed at 0° C. with 96% sulfuric acid (0.44 ml). To this end, a solution of 1,2,3,3a,5,9b-hexahydrocyclopenta[c]quinolin-4-one (1.9 g, 5.3 mmol) in dichloromethane (5 ml) is added in drops. After 1 hour at room temperature, the batch is poured onto ice water, the solid is filtered off and washed with water. Column-chromatographic purification (SiO$_2$) of the filter residue with ethyl acetate-hexane yields 0.65 g (53%) of product.

$^1$H-NMR (CDCl$_3$): δ=1.65–1.82 (m, 3H), 2.13–2.25 (m, 2H), 2.36 (m, 2H), 3.04 (td, 1H), 3.38 (q, 1H), 6.91 (d, 1H), 8.09 (dd, 1H), 8.15 (d, 1H), 9.07 (br. s, 1H).

8-Nitro-1,2,3,3a,5,9b-hexahydrocyclopenta[c] quinoline-4-thione

As described for Example 4, 8-nitro-1,2,3,3a,5,9b-hexahydrocyclopenta[c]quinolin-4-one (100 mg, 0.43 mmmol) is reacted with Lawesson's reagent (470 m hg, 1.16 mol) to form 100 hng (94%) of product.

$^1$H-NMR ([D$_6$]-DMSO): δ=1.51–1.78 (m, 3H), 2.09–2.28 (m, 3H), 3.47 (m, 2H), 7.31 (d, 1H), 8.14 (dd, 1H), 8.20 (d, 1H), 12.62 (br. s, 1H).

4-Amino-8-nitro-2,3,3a,9b-tetrahydro-1H-cyclopenta[c]quinoline

As described for Example 4, 8-nitro-1,2,3,3a,5,9b-hexahydrocyclopenta[c]quinoline-4-thione (100 mg, 0.40 mmol) is reacted with 7N methanolic ammonia solution (15 ml) to form 70 mg (76%) of product.

$^1$H-NMR ([D$_6$]-DMSO): δ=1.49–1.68 (m, 3H), 1.87 (m, 1H), 2.01–2.28 (m, 2H), 2.75 (q, 1H), 3.32 (q, 1H), 6.90 (d, 1H), 7.46 (br., 2H), 7.92 (dd, 1H), 7.99 (d, 1H).

EXAMPLE 7

4-Amino-2-oxa-2,3,3a,9b-hexahydro-1H-cyclopenta[c]quinoline

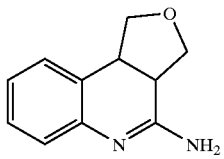

3-(Trifluoromethylsulfonyloxy)-2,5-dihydrofuran-4-carboxylic acid methyl ester A solution of tetrahydrofuran-3-one-4-carboxylic acid-methyl ester (P. Dowd, S.-C. Choi, Tetrahedron 1991, 47, 4847) (2.88 g, 20 mmol) in dichloromethane (200 ml) is mixed at −78° C. with diisopropyl(ethyl)amine (3.96 ml, 23.2 mmol). After 10 minutes, trifluoromethanesulfonic acid anhydride (3.88 ml, 23.2 mmol) is slowly added in drops to it. The batch is warmed to room temperature, stirred for 2 hours and concentrated by evaporation. The residue is purified by column chromatography ($SiO_2$) with ethyl acetate-hexane: 3.62 g (66%) of product.

$^1$H-NMR ($CDCl_3$): δ=3.85 (s, 3H), 4.80 (t, 2H), 4.92 (t, 2H).

2-Oxa-1,2,3,5-tetrahydrocyclopenta[c]quinolin-4-one 2-(Pivaloylamino)phenylboric acid (F. Guiller, F. Nivoliers, A. Godard, F. Marsais, G. Quéguiner, M. A. Siddiqui, V. Snieckus, J. Org. Chem. 1995, 60, 292) (0.66 g, 3.0 mmol), 3-(trifluoromethylsulfonyloxy)-2,5-dihydrofuran-4-carboxylic acid-methyl ester (0.69 g, 2.5 mmol), tetrakis(triphenylphosphine)palladium (69 mg, 0.06 mmol) and a 2M aqueous $Na_2CO_3$ solution (1.26 ml, 2.52 mmol) are refluxed in DME (40 ml) for 2.5 hours. The batch is diluted with ethyl acetate, washed with water and saturated NaCl, dried ($Na_2SO_4$) and concentrated by evaporation in a vacuum. Column chromatography on silica gel with ethyl acetate-hexane yields 0.65 g (87%) of 4-(2-(pivaloylamino)phenyl)-2,5-dihydrofuran-3-carboxylic acid-methyl ester (flash point 105–6° C.). 0.59 g (1.94 mmol) of it is then refluxed in concentrated hydrochloric acid for 2 hours. The batch is poured onto ice and extracted with ethyl acetate and dichloromethane. After drying ($Na_2SO_4$) and concentration by evaporation, the residue is heated for two more hours with concentrated HCl and worked up as described: 0.22 g (58%) of product.

$^1$H-NMR ($[D_6]$-DMSO): δ=4.98 (t, 2H), 5.31 (t, 2H), 7.22 (t, 1H), 7.42 (d, 1H), 7.48 (d, 1H), 7.53 (d, 1H), 11.78 (br., 1H).

2-Oxa-1,2,3,3a,5,9b-hexahydrocyclopenta[c]quinolin-4-one

A solution of 2-oxa-1,2,3,5-tetrahydrocyclopenta[c]quinolin-4-one (0.22 g, 1.17 mmol) in methanol (24 ml) is mixed with magnesium (0.28 g, 11.7 mmol) and acetic acid (0.02 ml). After 6 hours, an additional portion of magnesium (0.28 g, 11.7 mmol) is added to it and stirred for 12 hours at room temperature. The batch is filtered via a glass filter with ethyl acetate and methanol as eluants. The filtrate is concentrated by evaporation and purified by column chromatography ($SiO_2$) with ethyl acetate-methanol: 31 mg (14%) of product.

$^1$H-NMR ($CDCl_3$): δ=3.26 (ddd, 1H), 3.54 (t, 1H), 3.65 (q, 1H), 4.23 (t, 2H), 4.27 (dd, 1H), 4.43 (dd, 1H), 6.78 (d, 1H), 7.04 (t, 1H) 7.21 (d, 1H), 7.23 (t, 1H), 7.79 (br, 1H).

2-Oxa-1,2,3,3,3a,5,9b-hexahydrocyclopenta[c]quinoline-4-thione

As described for Example 4, 2-oxa-1,2,3,3a,5,9b-hexahydrocyclopenta[c]quinolin-4-one (53 mg, 0.28 mmol) is reacted with Lawesson's reagent (121 mg, 0.30 mmol) to form 31 mg (54%) of product.

$^1$H-NMR ($CDCl_3$): δ=3.65 (m, 2H), 3.70 (t, 1H), 4.32 (m, 2H), 4.50 (t, 1H), 6.86 (d, 1H), 7.14 (t, 1H), 7.21–7.31 (m, 2H), 9.50 (br., 1H).

4-Amino-2-oxa-2,3,3a,9b-tetrahydro-1H-cyclopenta[c]quinoline

As described for Example 4, 2-oxa-1,2,3,3a,5,9b-hexahydrocyclopenta[c]quinoline-4-thione (26 mg, 0.13 mmol) is reacted with 7N methanolic ammonia solution (10 ml) to form 23 mg (97%) of product.

$^1$H-NMR ($[D_6]$-DMSO): δ=3.31 (m, 1H), 3.58–3.75 (m, 3H), 4.18–4.26 (m, 2H), 6.97 (t, 1H), 6.99 (d, 1H), 7.14 (t, 1H), 7.18 (d, 1H), 8.40 (br., 2H);

MS (EI) m/e=188 ($M^+$).

EXAMPLE 8

4-Amino-7-methoxy-2,3,3a,9b-tetrahydro-1H-cyclopenta[c]quinoline

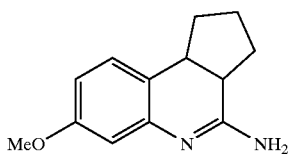

7-Methoxy-1,2,3,5-tetrahydrocyclopenta[c]quinolin-4-one

A solution of 3-methoxyphenylisocyanate (25.0 g, 168 mmol) in chloroform (110 ml) is mixed with 1-morpholino-1-cyclopentene (25.3 ml, 168 mmol) and refluxed for 15 minutes. The batch is concentrated by evaporation and purified by column chromatography ($SiO_2$) with ethyl acetate-hexane: 34.8 g (87%) of cyclopentanone-2-carboxylic acid-(3-methoxyphenyl)amide: $^1$H-NMR ($CDCl_3$): δ=1.80–2.55 (m, 6H), 3.18 (t, 1H), 3.81 (s, 3H), 6.68 (dd, 1H), 7.04 (ddd, 1H), 7.22 (t, 1H), 7.33 (t, 1H), 8.76 (br. s, 1H). The amide (11.6 g, 50 mmol) is stirred in concentrated sulfuric acid (40 ml) for 30 minutes at 100° C. The batch is poured onto ice water, diluted with water and extracted with ethyl acetate. The combined extracts are dried ($Na_2SO_4$) and concentrated by evaporation in a vacuum: 2.43 g (23%) of product.

$^1$H-NMR ($CDCl_3$): δ=2.08 (pent, 2H), 2.73 (t, 2H), 3.06 (t, 2H), 3.81 (s, 3H), 6.82 (dd, 1H), 6.87 (d, 1H), 7.46 (d, 1H), 11.47 (br. s, 1H).

7-Methoxy-1,2,3,3a,5,9b-hexahydrocyclopenta[c]quinolin-4-one 7-methoxy-1,2,3,5-tetrahydrocyclopenta[c]quinolin-4-one (400 mg, 1.86 mmol) and magnesium (452 mg, 18.6 mmol) are converted into 180 mg (45%) of product analogously to Example 7.

¹H-NMR (CDCl₃): δ=1.57–1.78 (m, 3H), 2.00–2.18 (m, 2H), 2.29 (m, 1H), 2.93 (td, 1H), 3.22 (q, 1H), 3.79 (s, 3H), 6.32 (d, 1H), 6.57 (dd, 1H), 7.11 (d, 1H), 8.19 (br. s, 1H).

7-Methoxy-1,2,3,3a,5,9b-hexahydrocyclopenta[c]quinoline-4-thione

Analogously to Example 4, 7-methoxy-1,2,3,3a,5,9b-hexahydrocyclopenta[c]quinolin-4-one (180 mg, 0.83 mmol) is reacted with Lawesson's reagent (370 mg, 0.91 mmol) to form 150 mg (78%) of product.

¹H-NMR (CDCl₃) δ=1.60–1.76 (m, 2H), 1.92 (m, 1H), 2.04–2.21 (m, 2H), 2.31 (m, 1H), 3.28 (m, 2H), 3.81 (s, 3H), 6.41 (d, 1H), 6.68 (dd, 1H), 7.16 (d, 1H), 9.79 (br. s, 1H).

4-Amino-7-methoxy-2,3,3a,9b-tetrahydro-1H-cyclopenta[c]quinoline

Analogously to Example 4, 7-methoxy-1,2,3,3a,5,9b-hexahydrocyclopenta[c]quinoline-4-thione (150 mg, 0.64 mmol) in 7N methanolic ammonia solution (25 ml) is reacted to form 110 mg (79%) of product.

¹H-NMR (CDCl₃): δ=1.50–1.76 (m, 3H), 1.94 (m, 1H), 2.09 (m, 1H), 2.30 (m, 1H), 3.10–3.27 (m, 2H), 3.73 (s, 3H), 6.56 (dd, 1H), 6.73 (d, 1H), 6.99 (d, 1H);

MS (EI) m/e=216 (M⁺).

EXAMPLE 9

4-Anino-8-methoxy-2,3,3a,9b-tetrahydro-1H-cyclopenta[c]quinoline

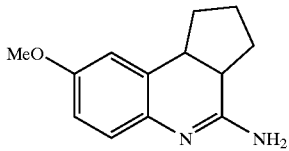

8-Methoxy-1,2,3,5-tetrahydrocyclopenta[c]cquinolin-4-one 7.10 g of cyclopentanone-2-carboxylic acid-(4-methoxyphenyl)amide (G. Jager, Chem. Ber. 1972, 105, 137) is stirred in concentrated sulfuric acid (20 ml) for 30 minutes at 100° C. The batch is poured onto ice water, diluted with water and extracted with ethyl acetate. The combined extracts are dried (Na₂SO₄) and concentrated by evaporation in a vacuum: 0.78 g (12%) of product.

¹H-NMR (CDCl₃): δ=2.12 (pent, 2H), 2.78 (t, 2H), 3.09 (t, 2H), 3.82 (s, 3H), 7.00 (d, 1H), 7.11 (dd, 1H), 7.29 (d, 1H), 11.42 (br. s, 1H).

8-Methoxy-1,2,3,3a,5,9b-hexahydrocyclopenta[c]quinolin-4-one

8-Methoxy-1,2,3,5-tetrahydrocyclopenta[c]quinolin-4-one (0.78 g, 3.6 mmol) and magnesium (2.5 g, 103 mmol) are reacted to form 80 mg (10%) of product analogously to Example 7.

¹H-NMR (CDCl₃): δ=1.59–1.79 (m, 3H), 2.03–2.48 (m, 3H), 2.94 (td, 1H), 3.23 (q, 1H), 3.79 (s, 3H), 6.67–6.78 (m, 3H), 8.13 (br. s, 1H).

8-Methoxy-1,2,3,3a,5,9b-hexahydrocyclopenta[c]quinoline-4-thione

Analogously to Example 4, 8-methoxy-1,2,3,3a,5,9b-hexahydrocyclopenta[c]quinolin-4-one (8 mg, 0.37 mmol) is reacted with Lawesson's reagent (404 mg, 1.0 mmol) to form 61 mg (71%) of product.

¹H-NMR (CDCl₃): δ=1.62–1.76 (m, 2H), 1.94 (m, 1H), 2.11–2.39 (m, 3H), 3.28 (m, 2H), 3.82 (s, 3H), 6.72 (dd, 1H), 6.89 (d, 1H), 6.81 (d, 1H), 9.84 (br. s, 1H).

4-Amino-8-methoxy-2,3,3a,9b-tetrahydro-1H-cyclolenta[c]quinoline

Analogously to Example 4, 8-methoxy-1,2,3,3a,5,9b-hexahydrocyclopenta[c]quinoline-4-thione (54 mg, 0.23 mmol) in 7N methanolic ammonia solution is reacted to form 23 mg (46%) of product.

¹H-NMR ([D₆]-DMSO): δ=1.44–1.62 (m, 3H), 1.87 (m, 1H), 1.98–2.15 (m, 2H), 2.66 (q, 1H), 3.19 (q, 1H), 3.69 (s, 3H), 6.62 (dd, 1H), 6.70 (d, 1H), 6.74 (br., 2H), 6.78 (d, 1H), MS (EI) m/e=216 (M⁺).

EXAMPLE 10

4-Amino-7-methyl-2,3,3a,9b-tetrahydro-1H-cyclopenta[c]quinoline

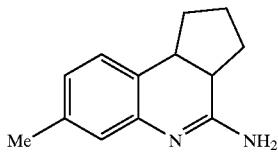

7-Methyl-2,3,3,3a,5,9b-hexahydrocyclopenta[c]quinolinne

7-Methyl-1,2,3,5-tetrahydrocyclopenta[c]quinolin-4-one (R. J. Brown, F. W. S. Carver, B. L. Hollingsworth, J. Chem. Soc. 1961, 4295) (800 mg, 4.0 mmol) and magnesium (975 mg, 40 mmol) are converted into 500 mg (62%) of product analogously to Example 7.

¹H-NMR (CDCl₃): δ=1.59–1.79 (m, 3H), 2.03–2.19 (m, 2H), 2.30 (m, 1H), 2.31 (s, 3H), 2.95 (td, 1H), 3.25 (q, 1H), 6.60 (s, 1H), 6.82 (d, 1H), 7.10 (d, 1H), 8.39 (br. s, 1H).

7-Methyl-1,2,3,3a,5,9b-hexahydrocyclopenta[c]quinoline-4-thione

Analogously to Example 4, 7-methyl-1,2,3,3a,5,9b-hexahydrocyclopenta[c]quinolin-4-one (200 mg, 1.0 mmol) is reacted with Lawesson's reagent (425 mg, 1.1 mmol) to form 230 mg of product.

¹H-NMR (CDCl₃): δ=1.60–1.75 (m, 2H), 1.93 (m, 1H), 2.07–2.34 (m, 3H), 2.32 (s, 3H), 3.29 (m, 2H), 6.68 (s, 1H), 6.93 (d, 1H), 7.14 (d, 1H), 9.98 (br. s, 1H).

4-Amino-7-methyl-2,3,3a,9b-tetrahydro-1H-cyclopenta[c]quinoline

In a way that is similar to Example 4, 7-methyl-1,2,3,3a, 5,9b-hexahy drocyclopenta[c]quinoline-4-thione (230 mg, 1.05 mmol) in 7N methanolic ammonia solution (25 ml) is reacted to form 210 mg (99%) of product.

¹H-NMR (CDCl₃): δ=1.51–1.78 (m, 3H), 1.94 (m, 1H), 2.03–2.33 (m, 2H), 2.23 (s, 3H), 3.05 (q, 1H), 3.24 (q, 1H), 6.17 (br., 2H), 6.81 (d, 1H), 6.93 (s, 1H), 7.00 (d, 1H).

MS (EI) (m/e)=200 (M⁺).

EXAMPLE 11

4-Amino-8-methyl-2,3,3a,9b-tetrahydro-1H-cyclolpenta[c]quinoline

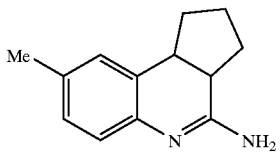

8-Methyl-1,2,3,3a,5,9b-hexahydrocyclopenta[c]quinolin-4-one

8-Methyl-1,2,3,5-tetrahydrocyclopenta[c]quinolin-4-one (R. J. Brown, F. W. S. Carver, B. L. Hollingsworth, J. Chem. Soc. 1961, 4295) (1.20 g, 6.0 mmol) and magnesium (1.46 g, 60 mmol) are converted into 0.48 g (40%) of product analogously to Example 7.

$^1$H-NMR (CDCl$_3$): δ=1.48–1.80 (m, 3H), 2.03–2.18 (m, 2H), 2.29 (s, 3H), 2.33 (s, 1H), 2.94 (td, 1H), 3.23 (q, 1H), 6.68 (d, 1H), 6.97 (d, 1H), 7.02 (s, 1H), 8.44 (br. s, 1H).

8-Methyl-1,2,3,3a,5,9b-hexahydrocyclopenta[c]quinoline-4-thione

Analogously to Example 4, 8-methyl-2,3,3a,5,9b-hexahydrocyclopenta[c]quinolin-4-one (200 mg, 1.0 mmol) is reacted with Lawesson's reagent (425 mg, 1.1 mmol) to form 210 mg (97%) of product.

$^1$H-NMR (CDCl$_3$): δ=1.62–1.75 (m, 2H), 1.91 (m, 1H), 2.07–2.38 (m, 3H), 2.31 (s, 3H), 3.28 (m, 2H), 6.75 (d, 1H), 6.99 (d, 1H), 7.06 (s, 1H), 9.87 (br. s, 1H).

4-Amino-8-2-methyl-2,3,3a,9b-tetrahydro-1H-cyclopenta[c]quinoline

In a way that is similar to Example 4, 8-methyl-1,2,3,3a5,9b-hexahydrocyclopenta[c]quinoline-4-thione (200 mg, 0.92 mmol) in 7N methanolic ammonia solution (20 ml) is reacted to form 190 mg (99%) of product.

$^1$H-NMR (CDCl$_3$) δ=1.52–1.78 (m, 3H), 1.91 (m, 1H), 2.07–2.35 (m, 2H), 2.25 (s, 3H), 3.11 (q, 1H), 3.22 (q, 1H), 6.27 (br., 2H), 6.87 (s, 1H), 6.88 (d, 1H), 7.02 (d, 1H);

MS (EI) m/e=200 (M$^+$)

EXAMPLE 12

4-Amino-8-chloro-2,3,3a,9b-tetrahydro-1H-cyclopenta[c]quinoline

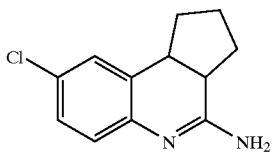

8-Chloro-1,2,3a,5,9b-hexahydrocyclopenta[c]quinolin-4-one

A solution of 1,2,3,3a,5,9b-hexahydrocyclopenta[c]quinolin-4-one (1.12 g, 6.0 mmol) and N-chlorosuccinimide (0.80 g, 6.0 mmol) in DMF (60 ml) is heated to 100° C. for 48 hours, poured onto ice water and extracted with ethyl acetate. The combined extracts are washed with 10% sulfuric acid and water, dried (Na$_2$SO$_4$) and concentrated by evaporation in a vacuum. The residue is purified on silica gel with ethyl acetate-hexane: 0.55 g (84%) of product.

$^1$H-NMR (CDCl$_3$): δ=1.60–1.82 (m, 3H), 2.05–2.22 (m, 2H), 2.32 (m, 1H), 2.95 (td, 1H), 3.25 (q, 1H), 6.76 (d, 1H), 7.13 (dd, 1H), 7.19 (d, 1H), 8.89 (br. s, 1H).

8-Chloro-4-methoxy-2,3,3a,9b-tetrahydro-1H-cyclopenta[c]quinoline

A solution of 8-chloro-1,2,3,3a,5,9b-hexahydrocyclopenta[c]quinolin-4-one (200 mg, 0.9 mmol) in dichloromethane (20 ml) is stirred with trimethyloxonium tetrafluoroborate (134 mg, 0.9 mmol) for 24 hours at room temperature. After triethylamine (0.13 ml, 0.9 mmol) is added, the batch is concentrated by evaporation and purified by column chromatography (SiO$_2$, 40% moist) with ethyl acetate-hexane: 180 mg (85%) of product.

$^1$H-NMR (CDCl$_3$): δ=1.57–1.78 (m, 3H), 1.93 (m, 1H), 2.07–2.23 (m, 2H), 2.84 (ddd, 1H), 3.28 (q, 1H), 3.88 (s, 3H), 7.07–7.18 (m, 3H).

4-Amino-8-chloro-2,3,3a,9b-tetrahydro-1H-cyclorenta[c]quinoline

A suspension of 8-chloro-4-methoxy-2,3,3a,9b-tetrahydro-1H-cyclopenta[c]quinoline (180 mg, 0.76 mmol) and ammonium chloride (200 mg, 3.81 mmol) in ethanol (15 ml) is refluxed for 8 hours and left for three days at room temperature. The solvent is distilled off, and the residue is purified on silica gel with dichloromethane-methanol: 50 mg (30%) of product.

$^1$H-NMR ([D$_6$]-DMSO): δ=1.48–1.77 (m, 3H), 2.02 (m, 1H), 2.13–2.28 (m, 2H), 3.21 (q, 1H), 3.47 (q, 1H), 7.16 (d, 1H), 7.33 (dd, 1H), 7.44 (d, 1H), 9.63 (br., 2H);

MS (EI) m/e=220 (M$^+$)

EXAMPLE 13

4-Amino-6,8-dichloro-2,3,3a,9b-tetrahydro-1H-cyclopenta[c]quinoline

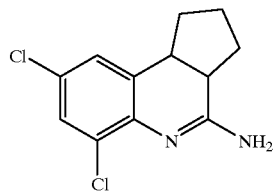

6,8-Dichloro-1,2,3,3a,5,9b-hexahydrocyclopenta[c]quinolin-4-one

A solution of 1,2,3,3a,5,9b-hexahydrocyclopenta[c]quinolin-4-one (300 mg, 1.6 mmol) in DMF (20 ml) is mixed with N-chlorosuccinimide (641 mg, 4.8 mmol), and it is stirred for 24 hours at 100° C. The batch is poured onto ice water and extracted with ethyl acetate. The combined extracts are washed with 10% sulfuric acid and water, dried (Na$_2$SO$_4$) and concentrated by evaporation in a vacuum. The residue is purified on silica gel with ethyl acetate-hexane: 350 mg (85%) of product.

$^1$H-NMR (CDCl$_3$): δ=1.55–1.84 (m, 3H), 2.03–2.19 (m, 2H), 2.38 (m, 1H), 2.97 (td, 1H), 3.25 (q, 1H), 7.13 (d, 1H), 7.25 (d, 1H), 7.77 (br. s, 1H).

6,8-Dichloro-1,2,3,3a,5,9b-hexahydrocyclopenta[c]quinoline-4-thione 6,8-Dichloro-1,2,3,3a,5,9b-hexahydrocyclopenta[c]quinolin-4-one (100 mg, 0.39 mmol) is heated with Lawesson's reagent (412 mg, 1.02 mmol) for 2 hours in THF (20 ml). The batch is concentrated by evaporation and purified by column chromatography (SiO$_2$) with ethyl acetate-hexane: 100 mg (94%) of product.

$^1$H-NMR (CDCl$_3$): δ=1.67–1.79 (m, 2H), 1.85 (m, 1H), 2.16 (m, 1H), 2.25–2.38 (m, 2H), 3.29 (m, 2H), 7.16 (d, 1H), 7.27 (d, 1H), 9.57 (br. s, 1H)

4-Amino-6,8-dichloro-2,3,3a,9b-tetrahydro-1H-cyclopenta[c]quinoline

Analogously to Example 4, 6,8-dichloro-1,2,3,3a,5,9b-hexahydrocyclopenta[c]quinoline-4-thione (100 mg, 0.37 mmol) is reacted with 7N methanolic ammonia solution (20 ml) to form 70 mg (74%) of product.

$^1$H-NMR ([D$_6$]-DMSO): δ=1.46–1.68 (m, 3H), 1.82 (m, 1H), 2.00–2.16 (m, 2H), 2.69 (q, 1H), 3.23 (q, 1H), 6.88 (br., 2H), 7.11 (d, 1H), 7.21 (d, 1H);

MS (EI) m/e=254 (M$^+$).

EXAMPLE 14

4-Amino-8-bromo-2,3,3a,9b-tetrahydro-1H-cyclopenta[c]quinoline

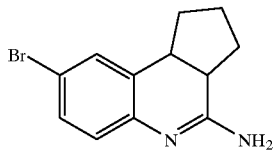

8-Bromo-1,2,3,3a,5,9b-hexahydrocyclopenta[c]quinolin-4-one

A solution of 1,2,3,3a,5,9b-hexahydrocyclopenta[c]quinolin-4-one (374 mg, 2.0 mmol) in DMF (10 ml) is mixed with N-bromosuccinimide (356 mg, 2.0 mmol). After 15 minutes of stirring at room temperature, the batch is heated for 15 minutes to 100° C., diluted with water and extracted with methyl-tert-butyl ether. The combined extracts are dried (Na$_2$SO$_4$) and concentrated by evaporation in a vacuum. The residue is purified on silica gel with ethyl acetate-hexane: 470 mg (88%) of product.

Flash point 170–2° C.

8-Brono-1,2,3,3a,5,9b-hexahydrocycloipenta[c]quinoline-4-thione

8-Bromo-1,2,3,3a,5,9b-hexahydrocyclopenta[c]quinolin-4-one (100 mg, 0.38 mmol) is heated with Lawesson's reagent (404 mg, 1.0 mmol) for 5 hours in THF (20 ml). The batch is concentrated by evaporation and purified by column chromatography (SiO$_2$) with ethyl acetate-hexane: 82 mg (76%) of product.

$^1$H-NMR (CDCl$_3$-[D$_6$]-DMSO): δ=1.49 (m, 2H), 1.72 (m, 1H), 1.90–2.16 (m, 3H), 3.05 (m, 2H), 6.83 (d, 1H), 7.07 (dd, 1H), 7.16 (d, 1H), 11.58 (br. s, 1H).

4-Amino-8-bromo-2,3,3a,9b-tetrahydro-1H-cycloipenta[c]quinoline

Analogously to Example 4, 8-bromo-1,2,3,3a,5,9b-hexahydrocyclopenta[c]quinoline-4-thione (76 mg, 0.30 mmol) is reacted with 7N methanolic ammonia solution (20 ml) to form 67 mg (84%) of product.

Flash point 171–3° C.;

MS (EI) m/e=264/266 (M$^+$).

EXAMPLE 15

4-Amino-8-(trifluoromethyl)-2,3,3a,9b-tetrahydro-1H-cyclopenta[c]quinoline

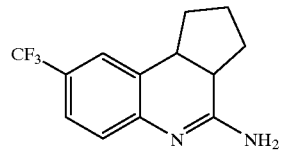

Pivalic acid-(4-trifluoromethyl)anilide

A solution of 4-(trifluoromethyl)aniline (6.3 ml, 50 mmol) in dichloromethane (200 ml) is mixed with 4-(dimethylamino)pyridine (30 mg), pyridine (12 ml, 150 mmol) and carefully mixed with pivaloyl chloride (9.2 ml, 75 mmol). After the exothermic reaction dies down, it is stirred for another 4 hours at room temperature before water (50 ml) is added to it. After 45 minutes, the batch is diluted with methyl-tert-butyl ether (300 ml), washed with 10% sulfuric acid (2×100 ml), dried (Na$_2$SO$_4$) and concentrated by evaporation in a vacuum. The residue is recrystallized from hexane: 12.09 g (99%) of product.

Flash point 157–8° C.

1-(Trifluoromethylsulfonyloxy)cyclopent-1-ene-2-carboxylic acid-ethyl ester

A solution of cyclopentanone-2-carboxylic acid-ethyl ester (7.2 ml, 50 mmol) in dichloromethane (200 ml) is mixed at −70° C. with triethylamine (7.6 ml, 55 mmol). After 10 minutes, trifluoromethanesulfonic acid anhydride (8.2 ml, 50 mmol) is slowly added in drops to it. The batch is stirred for 5 hours while being heated to room temperature, diluted with methyl-tert-butyl ether, washed with water and saturated NaCl, dried (Na$_2$SO$_4$) and concentrated by evaporation in a vacuum. The residue is purified by column chromatography (SiO$_2$) with ethyl acetate-hexane: 12.53 g (87%) of product.

$^1$H-NMR (CDCl$_3$): δ=1.33 (t, 3H), 2.03 (pent, 1H), 2.74 (m, 4H), 4.28 (q, 2H).

8-(Trifluoromethyl)-1,2,3,5-tetrahydrocyclopenta[c]quinolin-4-one

A solution of pivalic acid-(4-trifluoromethyl)anilide (3.68 g, 15 mmol) in THF (50 ml) is treated at 0° C. with 1.6 M of n-BuLi in hexane (28.2 ml, 45 mmol). After 4 hours of stirring at 0° C., boric acid-trimethylorthoester (5.1 ml, 45 mmol) is added to it and stirred for 2 hours at 0° C. The batch is diluted with water, acidified with 10% sulfuric acid and extracted with ethyl acetate. The combined extracts are dried and concentrated by evaporation in a vacuum. The residue (4.01 g) is refluxed with 1-(trifluoromethylsulfonyloxy)cyclopent-1-ene-2-carboxylic acid ethyl ester (2.3 g, 7.8 mmol), tetrakis(triphenylphosphine)palladium (0.2 g, 0.18 mmol) and 1 M aqueous Na$_2$CO$_3$ (7.8 ml, 7.8 mmol) in 1,2-dimethoxyethane (60 ml) for 4 hours. The reaction mixture is diluted with methyl-tert-butyl ether (300 ml), washed with water and saturated NaCl, dried (Na$_2$SO$_4$) and concentrated by evaporation in a vacuum. Column chromatography on silica gel with methyl-tert-butyl ether-hexane yields 4.7 g (82%) of 2-[2-(pivaloylamino)-5-(trifluoromethyl)phenyl]-cyclopent-1-ene-1-carboxylic acid-ethyl ester (selected $^1$H-NMR data (CDCl$_3$): δ=1.06 (t, 3H), 2.07 (pent, 2H), 2.79 (t, 2H), 2.90 (t, 2H), 4.05 (q, 2H)). 2.0 g (5.2 mmol) is refluxed in concentrated hydrochloric acid for 6 hours. The batch is poured onto ice water and filtered. The filter residue is washed with water: 1.08 g (82%) of product.

$^1$H-NMR ([D$_6$]-DMSO): δ=2.14 (pent, 2H), 2.81 (t, 2H), 3.16 (t, 2H), 7.52 (d, 1H), 7.78 (d, 1H), 7.87 (s, 1H), 11.89 (br. s, 1H).

8-(Trifluoromethyl)-1,2,3,3a,5,9b-hexahydrocyclopenta[c]quinolin4-one

Analogously to Example 7, 8-(trifluoromethyl)-1,2,3,5-tetrahydrocyclopenta[c]quinolin-4-one (1.08 g, 4.3 mmol) is reacted with magnesium (2.24 g, 92 mmol) to form 0.55 g (50%) of product.

$^1$H-NMR (CDCl$_3$): δ=1.58–1.81 (m, 3H), 2.06–2.22 (m, 2H), 2.32 (m, 1H), 2.99 (td, 1H), 3.31 (q, 1H), 6.84 (d, 1H), 7.42 (d, 1H), 7.47 (s, 1H), 8.87 (br. s, 1H).

8-(Trifluoromethyl)-1,2,3,3a,5,9b-hexahydrocyclopenta[c]quinoline-4-thione

Analogously to Example 4, 8-(trifluoromethyl)-1,2,3,3a,5,9b-hexahydrocyclopenta[c]quinolin-4-one (0.15 g, 0.6 mmol) is reacted with Lawesson's reagent (0.49 g, 1.2 mmol) to form 0.10 g (61%) of product.

$^1$H-NMR (CDCl$_3$): δ=1.66–1.81 (m, 2H), 1.92 (m, 1H), 2.13–2.42 (m, 3H), 3.33 (m, 2H), 6.92 (d, 1H), 7.47 (d, 1H), 7.53 (s, 1H), 9.73 (br. s, 1H).

4-Amino-8-(trifluoromethyl)-2,3,3a,9b-tetrahydro-1H-cyclopenta[c]quinoline

Analogously to Example 4, 8-(trifluoromethyl)-1,2,3,3a,5,9b-hexahydrocyclopenta[c]quinoline-4-thione (93 mg, 0.34 mmol) in 7N methanolic ammonia solution (20 ml) is reacted to form 66 mg (76%) of product.

Flash point 163–5° C.

$^1$H-NMR (CDCl$_3$): δ=1.63–2.01 (m, 4H), 2.22 (m, 2H), 2.81 (q, 1H), 3.35 (q, 1H), 5.12 (br., 2H), 7.07 (d, 1H), 7.37 (s, 1H) , 7.39 (d, 1H);

MS (EI) m/e=254 (M$^+$).

EXAMPLE 16

4-Amino-8-cyano-2,3,3a,9b-tetrahydro-1H-cyclopenta[c]quinoline

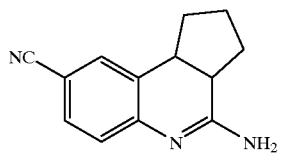

8-Cyano-1,2,3,3a,5,9b-hexahydrocyclopenta[c]quinolin-4-one

A solution of 8-bromo-1,2,3,3a,5,9b-hexahydrocyclopenta[c]quinolin-4-one (230 mg, 0.86 mmol) in DMF (20 ml) is mixed with copper(I) cyanide (77 mg, 0.86 mmol) and refluxed for 16 hours. The batch is diluted dichloromethane, washed with saturated NH$_4$Cl, dried (Na$_2$SO$_4$) and concentrated by evaporation in a vacuum. Purification on silica gel with ethyl acetate-hexane yields 70 mg (38%) of product.

$^1$H-NMR (CDCl$_3$): δ=1.57–1.82 (m, 3H), 2.09–2.25 (m, 2H), 2.34 (m, 1H), 3.01 (td, 1H), 3.30 (q, 1H), 6.89 (d, 1H), 7.48 (d, 1H), 7.50 (s, 1H), 9.14 (br. s, 1H).

8-Cyano-1,2,3,3a,5,9b-hexahydrocyclopenta[c]quinoline-4-thione

8-Cyano-1,2,3,3a,5,9b-hexahydrocyclopenta[c]quinolin-4-one (70 mg, 0.33 mmol) is heated to 80° C. with Lawesson's reagent (146 mg, 0.36 mmol) for 2 hours in DME (20 ml). The batch is concentrated by evaporation and purified by column chromatography (SiO$_2$) with ethyl acetate-hexane: 50 mg (66%) of product.

$^1$H-NMR (CDCl$_3$): δ=1.64–1.79 (m, 2H), 1.88 (m, 1H), 2.13–2.42 (m, 3H), 3.33 (m, 2H), 6.92 (d, 1H), 7.52 (d, 1H), 7.57 (s, 1H), 9.80 (br. s, 1H).

4-Amino-8-cyano-2,3,3a,9b-tetrahydro-1H-cyclopenta[c]quinoline

Analogously to Example 4, 8-cyano-1,2,3,3a,5,9b-hexahydrocyclopenta[c]quinoline-4-thione (40 mg, 0.18 mmol) is reacted with 7N methanolic ammonia solution (10 ml) to form 30 mg (81%) of product.

$^1$H-NMR ([D$_6$]-DMSO): δ=1.43–1.67 (m, 3H), 1.89 (m, 1H), 2.01–2.19 (m, 2H), 2.73 (q, 1H), 3.26 (q, 1H), 6.89 (d, 1H), 7.20 (br., 2H), 7.42 (d, 1H), 7.52 (s, 1H);

MS (EI) m/e=211 (M$^+$)

EXAMPLE 17

4-Amino-8-fluoro-2,3,3a,9b-tetrahydro-1H-cyclopenta[c]quinoline

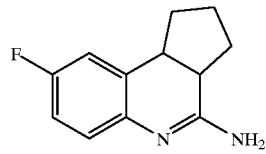

8-Fluoro-1,2,3,5-tetrahydrocyclopenta[c]quinolin-4-one

A solution of 4-fluorophenylisocyanate (5.0 g, 36.5 mmol) in chloroform (25 ml) is mixed with 1-morpholino-1-cyclopentene (5.5 ml, 36.5 mmol) and refluxed for 15 minutes. The batch is concentrated by evaporation and purified by column chromatography (SiO$_2$) with ethyl acetate-hexane: 7.6 g (94%) of cyclopentanone-2-carboxylic acid-(4-fluorophenyl)amide, 1H-NMR (DSC842). The amide is stirred in concentrated sulfuric acid (30 ml) for 30 minutes at 100° C. The batch is poured onto ice water and filtered. The filter residue is recrystallized from ethanol: 2.02 g (29%) of product.

Flash point 287° C.

8-Fluoro-1,2,3,3a,5,9b-hexahydrocyclopenta[c]quinolin-4-one

8-Fluoro-1,2,3,5-tetrahydrocyclopenta[c]quinolin-4-one (1.0 g, 4.9 mmol) and magnesium (1.2 g, 49.2 mmol) are reacted to form 280 mg (28%) of product analogously to Example 7.

$^1$H-NMR (CDCl$_3$): δ=1.60–1.80 (m, 3H), 2.05–2.20 (m, 2H), 2.31 (m, 1H), 2.94 (td, 1H), 3.25 (q, 1H), 6.75 (dd, 1H), 6.87 (td, 1H), 6.93 (dd, 1H), 8.69 (br. s, 1H).

8-Fluoro-1,2,3,3a,5,9b-hexahydrocyclopenta[c]
quinoline-4-thione

Analogously to Example 4, 8-fluoro-1,2,3,3a,5,9b-hexahydrocyclopenta[c]quinolin-4-one (280 mg, 1.36 mmol) is reacted with Lawesson's reagent (608 mg, 1.5 mmol) to form 240 mg (80%) of product.

$^1$H-NMR (CDCl$_3$): δ=1.59–1.77 (m, 2H), 1.90 (m, 1H), 2.10–2.25 (m, 2H), 2.32 (m, 1H), 3.29 (m, 2H), 6.82–6.92 (m, 2H), 6.97 (dd, 1H), 10.08 (br. s, 1H).

4-Amino-8-fluoro-2,3,3a,9b-tetrahydro-1H-cyclopenta[c]quinoline

Analogously to Example 4, 8-fluoro-1,2,3,3a,5,9b-hexahydrocyclopenta[c]quinoline-4-thione (240 mg, 1.08 mmol) in 7N methanolic ammonia solution (30 ml) is reacted to form 210 mg (95%) of product.

$^1$H-NMR ([D$_6$]-DMSO): δ=1.47–1.70 (m, 3H), 1.94 (m, 1H), 2.07–2.21 (m, 2H), 2.94 (q, 1H), 3.30 (br., 2H), 3.36 (q, 1H), 6.92–7.01 (m, 2H), 7.11 (dd, 1H);
MS (EI) m/e=204 (M$^+$).

EXAMPLE 18

4-Amino-7-fluoro-2,3,3a,9b-tetrahydro-1H-cyclopenta[c]quinoline

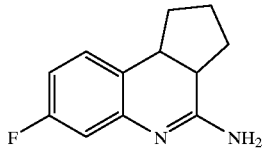

7-Fluoro-1,2,3,5-tetrahydrocyclopenta[c]quinolin-4-one

Analogously to Example 17, 1H-NMR (DSC841) is produced from 3-fluorophenylisocyanate (5.0 g, 36.5 mmol) and 1-morpholino-1-cyclopentene (5.5 ml, 36.5 mmol) of cyclopentanone-2-carboxylic acid-(3-fluorophenyl)amide (6.75 g, 84%). The amide is stirred into concentrated sulfuric acid (30 ml) for 30 minutes at 100° C. The batch is poured onto ice water and filtered. The filter residue is recrystallized from ethanol: 5.14 g (83%) of product.

Flash point 283° C.

7-Fluoro-1,2,3,3a,5,9b-hexahydrocyclopenta[c]
quinolin-4-one

7-Fluoro-1,2,3,5-tetrahydrocyclopenta[c]quinolin-4-one (1.0 g, 4.9 mmol) and magnesium (1.2 g, 49.2 mmol) are reacted to form 170 mg (17%) of product analogously to Example 7.

$^1$H-NMR (CDCl$_3$): δ=1.56–1.82 (m, 3H), 2.02–2.19 (m, 2H), 2.32 (m, 1H), 2.96 (td, 1H), 3.24 (q, 1H), 6.53 (dd, 1H); 6.70 (td, 1H), 7.14 (dd, 1H), 8.60 (br. s, 1H).

7-Fluoro-1,2,3,3a,5,9b-hexahydrocyclopenta[c]
quinoline-4-thione

Analogously to Example 4, 7-fluoro-1,2,3,3a,5,9b-hexahydrocyclopenta[c]quinolin-4-one (170 mg, 0.83 mmol) is reacted with Lawesson's reagent (370 mg, 0.91 mmol) to form 170 mg (93%) of product.

$^1$H-NMR (CDCl$_3$): δ=1.63–1.77 (m, 2H), 1.89 (m, 1H), 2.08–2.40 (m, 3H), 3.28 (m, 2H), 6.59 (dd, 1H), 6.82 (td, 1H), 7.21 (dd, 1H), 9.76 (br. s, 1H).

4-Amino-7-fluoro-2,3,3a,9b-tetrahydro-1H-cyclopenta[c]quinoline

Analogously to Example 4, 7-Fluoro-1,2,3,3a,5,9b-hexahydrocyclopenta[c]quinoline-4-thione (170 mg, 0.77 mmol) in 7N methanolic ammonia solution (20 ml) is reacted to form 160 mg (99%) of product.

$^1$H-NMR ([D$_6$]-DMSO): δ=1.43–1.72 (m, 3H), 1.90 (m, 1H), 2.07–2.21 (m, 2H), 2.96 (q, 1H), 3.30 (br., 2H), 3.32 (q, 1H), 6.76 (m, 1H), 6.81 (m, 1H), 7.24 (t, 1H).
MS (Ei) m/e=204 (M$^+$).

EXAMPLE 19

4-Amino-6-fluoro-2,3,3a,9b-tetrahydro-1H-cyclopenta[c]quinoline

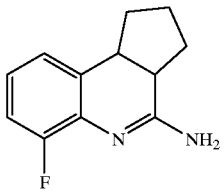

Pivalic acid-2-fluoroanilide

A solution of 2-fluoroaniline (4.8 ml, 50 mmol) in dichloromethane (200 ml) is mixed with pyridine (12 ml, 150 mmol) and carefully mixed with pivaloyl chloride (9.2 ml, 75 mmol). After the exothermic reaction has run its course, the batch is stirred for another hour at room temperature, diluted with methyl-tert-butyl ether, washed with 10% hydrochloric acid and saturated NaCl, dried (Na$_2$SO$_4$) and concentrated by evaporation in a vacuum. The residue is recrystallized from hexane: 4.86 g (50%) of product.

Flash point 77–8° C.

6-Fluoro-1,2,3,5-tetrahydrocyclopenta[c]quinolin-4-one

A solution of pivalic acid-2-fluoroanilide (3.68 g, 15 mmol) in THF (50 ml) is treated at 0° C. with 1.6 M of n-BuLi in hexane (28.2 ml, 45 mmol). After 2 hours of stirring at 0° C., boric acid-trimethylorthoester (5.1 ml, 45 mmol) is added to it, and it is stirred for two hours at 0° C. The batch is diluted with water, acidified with 10% sulfuric acid (pH 3) and extracted with ethyl acetate. The combined extracts are dried and concentrated by evaporation in a vacuum. The residue is refluxed for 4 hours with 1-(trifluoromethylsulfonyloxy)cyclopent-1-ene-2-carboxylic acid-ethyl ester (3.75 g, 1.30 mmol), tetrakis (triphenyl-phosphine)palladium (0.35 g, 0.3 mmol) and 1 M aqueous Na$_2$CO$_3$ (13.0 ml, 13.0 mmol) in 1,2-dimethoxyethane (100 ml). The reaction mixture is diluted with methyl-tert-butyl ether (300 ml), washed with water and saturated NaCl, dried (Na$_2$SO$_4$) and concentrated by evaporation in a vacuum. Column chromatography on silica gel with methyl-tert-butyl ether-hexane yields 4.7 g (82%) of 2-[2-(pivaloylamino)-3-fluorophenyl)-cyclopent-1-ene-1-carboxylic acid-ethyl ester, $^1$H-NMR (CDCl$_3$): δ=1.21 (t, 3H), 1.26 (s, 9H), 1.98 (pent, 2H), 2.80 (m, 4H), 4.12 (q, 2H), 6.93 (d, 1H), 7.07 (t, 1H), 7.20 (td, 1H), 7.58 (br. s, 1H). 1.0 g (3.0 mmol) in concentrated hydrochloric acid is refluxed for 6 hours. The batch is diluted with water and filtered: 494 mg (80%) of product.

¹H-NMR (CDCl₃): δ=2.23 (pent, 2H), 3.01 (t, 2H), 3.14 (t, 2H), 7.10–7.33 (m, 3H), 9.14 (br. s, 1H).

6-Fluoro-1,2,3,3a,5,9b-hexahydrocyclopenta[c]quinolin-4-one

Analogously to Example 7, 6-fluoro-1,2,3,5-tetrahydrocyclopenta[c]quinolin-4-one (494 mg, 2.4 mmol) is reacted with magnesium (1.22 g, 50.0 mmol) to form 280 mg (56%) of product.

¹H-NMR (CDCl₃): δ=1.58–1.81 (m, 3H), 2.12 (m, 2H), 2.32 (m, 21H), 2.98 (td, 1H), 3.31 (q, 1H), 6.91–7.07 (m, 3H), 7.67 (br. s, 1H).

6-Fluoro-1,2,3,3a,5,9b-hexahydrocyclopenta[c]quinoline-4-thione

A solution of 6-fluoro-1,2,3,3a,5,9b-hexahydrocyclopenta[c]quinolin-4-one (100 mg, 0.48 mmol) and Lawesson's reagent (512 mg, 1.26 mmol) in THF (20 ml) is refluxed for 1.5 hours and concentrated by evaporation. Column chromatography of the residue with ethyl acetate-hexane yields 100 mg (93%) of product.

¹H-NMR (CDCl₃): δ=1.62–1.80 (m, 2H), 1.93 (m, 1H), 2.12–2.40 (m, 3H), 3.32 (m, 2H), 6.92–7.06 (m, 3H), 9.46 (br. s, 1H).

4-Amino-6-fluoro-2,3,3a,9b-tetrahydro-1H-cyclopenta[c]quinoline

Analogously to Example 4, 6-fluoro-1,2,3,3a,5,9b-hexahydrocyclopenta[c]quinoline-4-thione (100 mg, 0.45 mmol) in 7N methanolic ammonia solution (15 ml) is reacted to form 59 mg (64%) of product.

¹H-NMR ([D₆]-DMSO): δ=1.45–1.71 (m, 3H), 1.87 (m, 1H), 2.01–2.17 (m, 2H), 2.68 (q, 1H), 3.22 (q, 1H), 6.53–6.97 (m, 5H);

MS (EI) m/e=204 (M⁺).

EXAMPLE 20

4-Amino-7-(2-furanyl)-2,3,3a,9b-tetrahydro-1H-cyclopenta[c]quinoline

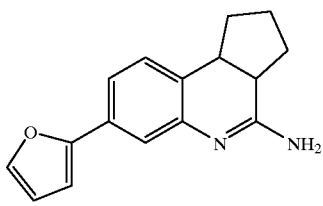

7-Bromo-1,2,3,5-tetrahydrocycloienta[c]quinolin-4-one

1-Morpholino-1-cyclopentene (15.2 ml, 101 mmol) is carefully added in drops to a solution of 3-bromophenylisocyanate (20.0 g, 101 mmol) in chloroform (100 ml). The batch is refluxed for 15 minutes and concentrated by evaporation in a vacuum. Column chromatography on silica gel with hexane-ethyl acetate yielded 25.0 g (88.6 mmol) of cyclopentan-2-one-1-carboxylic acid-(3-bromophenyl)amide. The latter are mixed with concentrated sulfuric acid (83 ml) and stirred for 30 minutes at 90° C. After cooling to room temperature, the batch is poured onto 600 g of ice, the precipitated solid is suctioned off and recrystallized from ethanol: 17.0 g of product.

¹H-NMR ([D₆]DMSO): δ=2.11 (pent, 2H), 2.74 (t, 2H), 3.07 (t, 2H), 7.34 (dd, 1H), 7.49 (d, 1H), 7.52 (d, 1H), 11.68 (s, H).

7-(2-Furanyl)-1,2,3,5-tetrahydrocyclopenta[c]quinolin-4-one

A suspension of 7-bromo-1,2,3,5-tetrahydrocyclopenta[c]quinolin-4-one (1.32 g, 5.0 mmol) in toluene (200 ml) is mixed with 2-(tributylstannyl)furan (1.7 ml, 5.5 mmol) and tetrakis(triphenylphosphine)palladium (0.29 g, 0.25 mmol). The reaction mixture is degassed, aerated with nitrogen, stirred for 15 hours at room temperature and heated for 4.5 hours to 110° C. The batch is mixed with silica gel and concentrated by evaporation in a vacuum. Column chromatography of the residue on silica gel with hexane-ethyl acetate yields 1.33 g of product.

¹H-NMR ([D₆]DMSO/CDCl₃): δ=2.00 (pent, 2H), 2.70 (t, 2H), 2.91 (t, 2H), 6.30 (dd, 1H), 6.58 (d, 1H), 7.22–7.31 (m, 3H), 7.44 (d, 1H), 11.09 (br. s, 1H).

7-(2-Furanyl)-1,2,3,3a,5,9b-hexahydrocycloienta[c]quinolin-4-one

A solution of 7-(2-furanyl)-1,2,3,5-tetrahydrocyclopenta[c]quinolin-4-one (1.32 g, 5.3 mmol) in methanol (300 ml) is mixed with magnesium (2.58 g, 10.6 mmol) and acetic acid (0.06 ml). After 15 hours at room temperature, another portion of magnesium (1.29 g, 5.3 mmol) is added to it. The batch is stirred for 15 hours at room temperature, treated with 10% hydrochloric acid (500 ml) and extracted with ethyl acetate (3×300 ml). The combined extracts are dried (Na₂SO₄) and concentrated by evaporation in a vacuum. Column chromatography on silica gel with hexane-ethyl acetate yields 0.49 g of product.

¹H-NMR (CDCl₃): δ=1.60–1.80 (m, 3H), 2.05–2.20 (m, 2H), 2.34 (m, 1H), 2.98 (td, 1H), 3.26 (q, 1H), 6.48 (dd, 1H), 6.64 (d, 1H), 7.04 (d, 1H), 7.22 (d, 1H), 7.32 (dd, 1H), 7.47 (d, 1H), 8.04 (br. s, 1H).

7-(2-Furanyl)-1,2,3,3a,5,9b-hexahydrocyclopenta[c]quinoline-4-thione

Analogously to Example 4, 7-(2-furanyl)-1,2,3,3a,5,9b-hexahydrocyclopenta[c]quinolin-4-one (100 mg, 0.39 mmol) is reacted with Lawesson's reagent (404 mg, 1.0 mmol) to form 103 mg (98%) of product.

¹H-NMR (CDCl₃): δ=1.63–1.77 (m, 2H), 1.95 (m, 1H), 2.09–2.41 (m, 3H), 3.32 (m, 2H), 6.48 (dd, 1H), 6.65 (d, 1H), 7.16 (d, 1H), 7.25 (d, 1H), 7.40 (dd, 1H), 7.47 (d, 1H), 9.86 (br. s, 1H).

4-Amino-7-(2-furanyl)-2,3,3a,9b-tetrahydro-1H-cyclopenta[c]quinoline

Analogously to Example 4, 7-(2-furanyl)-1,2,3,3a,5,9b-hexahydrocyclopenta[c]quinoline-4-thione (95 mg, 0.35 mmol) in 7N methanolic ammonia solution (30 ml) is reacted to form 72 mg (82%) of product.

¹H-NMR (CDCl₃): δ=1.58–1.85 (m, 3H), 1.96 (m, 1H), 2.07–2.33 (m, 2H), 2.91 (q, 1H), 3.32 (q, 1H), 4.61 (br., 2H), 6.43 (m, 1H), 6.61 (d, 1H), 7.15 (d, 1H), 7.31 (d, 1H), 7.35 (s, 1H), 7.43 (s, 1H);

MS (EI) m/e=252 (M⁺).

EXAMPLE 21

4-Amino-7-(4-morpholinyl)-2,3,3a,9b-tetrahydro-1H-cyclopenta[c]quinoline

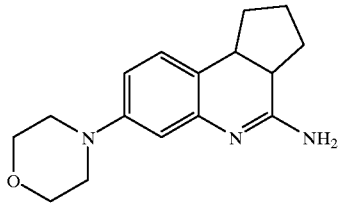

7-(4-Morpholinyl)-1,2,3,5-tetrahydrocyclopenta[c]quinolin-4-one

A solution of 1,1,1,3,3,3-hexamethyldisilazane (2.6 ml, 12.5 mmol) in toluene (100 ml) is mixed at 0° C. with 1.6 M of n-BuLi in hexane (7.5 ml, 12.0 mmol) and stirred for 15 minutes at 0° C. 7-Bromo-1,2,3,5-tetrahydrocyclopenta[c]quinolin-4-one (1.34 g, 5.0 mmol), morpholine (0.65 ml, 7.5 mmol), palladium dichloride (44 mg, 0.25 mmol) and tri-o-tolylphosphine (152 mg, 0.5 mmol) are added to it. The batch is refluxed for 5 hours, diluted with ethyl acetate, washed with saturated NaCl, dried ($Na_2SO_4$) and concentrated by evaporation in a vacuum. Purification of the residue on silica gel with dichloromethane-ethanol yields 1.17 g of product.

$^1$H-NMR ($CDCl_3$): δ=2.19 (pent, 2H), 2.96 (t, 2H), 3.07 (t, 2H), 3.27 (dd, 4H), 3.89 (dd, 4H), 6.73 (d, 1H), 6.83 (dd, 1H), 7.39 (d, 1H), 11.04 (br.s, 1H).

7-(4-Morpholinyl)-1,2,3,3a,5,9b-hexahydrocyclopenta[c]quinolin-4-one

Analogously to Example 7, 7-(4-morpholinyl)-1,2,3,5-tetrahydrocyclopenta[c]quinolin-4-one (1.17 g, 4.3 mmol) is converted with magnesium (2.16 g, 86.6 mmol) into 660 mg (56%) of product.

Flash point 210–12° C.

7-(4-Morpholinyl)-1,2,3,3a,5,9b-hexahydrocyclopenta[c]quinoline-4-thione

Analogously to Example 4, 7-(4-morpholinyl)-1,2,3,3a,5,9b-hexahydrocyclopenta[c]quinolin-4-one (100 mg, 0.37 mmol) is reacted with Lawesson's reagent (164 mg, 0.41 mmol) to form 90 mg (84%) of product.

Flash point 182° C.

4-Amino-7-(4-morpholinyl)-2,3,3a,9b-tetrahydro-1H-cyclopenta[c]quinoline

Analogously to Example 4, 7-(4-morpholinyl)-1,2,3,3a,5,9b-hexahydrocyclopenta[c]quinoline-4-thione (80 mg, 0.28 mmol) in 7N methanolic ammonia solution (15 ml) is reacted to form 40 mg (53%) of product.

$^1$H-NMR ($[D_5]$-pyridine): δ=1.43–1.61 (m, 2H), 1.87 (dq, 1H), 2.00 (m, 2H), 2.08 (dtd, 1H), 2.83 (q, 1H), 3.12 (dd, 4H), 3.26 (q, 1H), 3.76 (dd, 4H), 4.87 (br., 2H), 6.72 (dd, 1H), 7.12 (d, 1H), 7.17 (d, 1H);

MS (EI): m/e=271 (M$^+$)

EXAMPLE 22

4-Amino-7-(methoxycarbonylethyl)-2,3,3a,9b-tetrahydro-1H-cyclopenta[c]quinoline

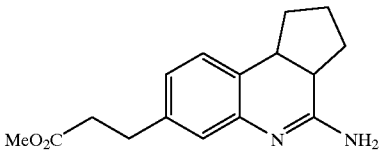

7-(Methoxycarbonylethenyl)-1,2,3,5-tetrahydrocyclopenta[c]quinolin-4-one

A suspension of 7-bromo-1,2,3,5-tetrahydrocyclopenta[c]quinolin-4-one (528 mg, 2.0 mmol), acrylic acid-methyl ester (0.36 ml, 4.0 mmol), tetrakis(triphenylphosphine)palladium (116 mg, 0.1 mmol) and triethylamine (0.56 ml, 4.0 mmol) in DMF (25 ml) is stirred for 3 hours at 120° C. The batch is diluted with ethyl acetate, washed with water, dried ($Na_2SO_4$) and concentrated by evaporation in a vacuum. Purification of the residue on silica gel with dichloromethane-ethanol yields 550 mg (99%) of product.

$^1$H-NMR ($[D_6]$-DMSO): δ=2.12 (pent, 2H), 2.80 (t, 2H), 3.12 (t, 2H), 3.77 (s, 3H), 6.61 (d, 1H), 7.52 (s, 1H), 7.56 (s, 2H), 7.67 (d, 1H), 11.19 (br.s, 1H).

7-(Methoxycarbonylethyl)-1,2,3,3a,5,9b-hexahydrocyclopenta[c]quinolin-4-one

A solution of 7-(methoxycarbonylethenyl)-1,2,3,5-tetrahydrocyclopenta[c]quinolin-4-one (550 mg, 2.0 mmol) in methanol-THF 3:1 (130 ml) is mixed with magnesium (972 mg, 40.0 mmol) and stirred for 24 hours at room temperature. The reaction mixture is filtered on spun glass, the filter residue is washed with dichloromethane-methanol, and the combined filtrates are concentrated by evaporation in a vacuum. Purification of the residue on silica gel yields 120 mg (22%) of product.

$^1$H-NMR ($CDCl_3$): δ=1.57–1.77 (m, 3H), 2.02–2.18 (m, 2H), 2.31 (m, 1H), 2.63 (t, 2H), 2.91 (t, 2H), 2.94 (td, 1H), 3.23 (q, 1H), 3.69 (s, 3H), 6.58 (d, 1H), 6.84 (dd, 1H), 7.12 (d, 1H), 8.11 (br.s, 1H).

7-(Methoxycarbonylethyl)-1,2,3,3a,5,9b-hexahydrocyclopenta[c]quinoline-4-thione Analogously to Example 4, 7-(methoxycarbonylethyl)-1,2,3,3a,5,9b-hexahydrocyclopenta[c]quinolin-4-one (120 mg, 0.44 mmol) is reacted with Lawesson's reagent (195 mg, 0.48 mmol) to form 150 mg of product.

$^1$H-NMR ($CDCl_3$): δ=1.60–1.75 (m, 2H), 1.92 (m, 1H), 2.08–2.23 (m, 2H), 2.32 (m, 1H), 2.64 (t, 2H), 2.93 (t, 2H), 3.28 (m, 2H), 3.69 (s, 3H), 6.72 (d, 1H), 6.96 (dd, 1H), 7.18 (d, 1H), 9.80 (br.s, 1H).

4-Amino-7-(methoxycarbonylethyl)-2,3,3a,9b-tetrahydro-1H-cyclopenta[c]quinoline Analogously to Example 4, 7-(methoxycarbonylethyl)-1,2,3,3a,5,9b-hexahydrocyclopenta[c]quinoline-4-thione (150 mg, 0.52 mmol) in 7N methanolic ammonia solution (20 ml) is reacted to form 40 mg (28%) of product.

$^1$H-NMR ($CDCl_3$): δ=1.61–1.80 (m, 3H), 1.92 (sept, 1H), 2.08–2.23 (m, 2H), 2.62 (t, 2H), 2.85 (q, 1H), 2.89 (t, 2H), 3.27 (q, 1H), 3.67 (s, 3H), 4.87 (br., 2H), 6.84 (dd, 1H), 6.89 (d, 1H), 7.06 (d, 1H);

MS (EI): m/e=272 (M$^+$)

EXAMPLE 23

4-Methylamino-2,3,3a,9b-tetrahydro-1H-cyclopenta[c]quinoline

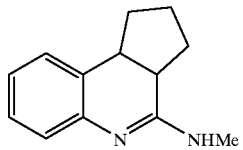

1,2,3,3a,5,9b-Hexahydrocyclopenta[c]quinoline-4-thione (90 mg, 0.44 mmol) is stirred in 2 M methanolic methylamine solution (15 ml) for 24 hours at room temperature. After concentration by evaporation, the residue is purified on silica gel with dichloromethane-methanol: 90 mg (99%).

$^1$H-NMR ([D$_6$]-DMSO): δ=1.42–1.69 (m, 3H), 1.92–2.17 (m, 3H), 2.74 (m, 1H), 2.89 (s, 3H), 3.27 (m, 1H), 6.91 (t, 1H), 7.02 (d, 1H), 7.08 (t, 1H), 7.17 (d, 1H);

MS (EI) m/e=200 (M$^+$).

EXAMPLE 24

4-Ethylamino-2,3,3a,9b-tetrahydro-1H-cycloienta[c]qquinoline

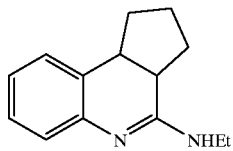

1,2,3,3a,5,9b-Hexahydrocyclopenta[c]quinoline-4-thione (90 mg, 0.44 mmol) is stirred in 2 M methanolic ethylamine solution (15 ml) for 24 hours at room temperature. After concentration by evaporation, the residue is purified on silica gel with dichloromethane-methanol: 60 mg (64%).

$^1$H-NMR ([D$_6$]-DMSO): δ==1.17 (t, 3H), 1.42–1.67 (m, 3H), 1.92–2.15 (m, 3H), 2.69 (m, 1H), 3.28 (m, 1H), 3.37 (q, 2H), 6.88 (t, 1H), 6.96 (d, 1H), 7.05 (t, 1H), 7.16 (d, 1H), MS (EI) m/e=214 (M$^+$).

EXAMPLE 25

4-Hydroxyamino-2,3,3a,9b-tetrahydro-1H-cyclopenta[c]quinoline or 1,2,3,3a,5,9b-hexahydrocyclopenta[c]quinolin-4-oxime A suspension of 1,2,3,3a,5,9b-hexahydrocyclopenta[c]quinoline-4-thione (50 mg, 0.25 mmol), hydroxylammonium sulfate (404 mg, 2.5 mmol) and triethylamine (0.38 ml, 2.7 mmol) in ethanol-THF 2:1 (15 ml) is stirred for 24 hours at room temperature. The solvent is distilled off, and the residue is purified on silica gel with hexane-ethyl acetate.

$^1$H-NMR ([D$_6$]-DMSO): δ1.51–1.77 (m, 3H), 1.87 (m, 1H), 1.95–2.08 (m, 2H), 2.81 (q, 1H), 3.15 (q, 1H), 6.81 (t, 1H), 7.05 (t, 1H), 7.10 (d, 1H), 7.16 (d, 1H), 8.60 (br., 1H), 9.51 (br., 1H).

Obtained analogously are:

4-Amino-7-hydroxy-2,3,3a,9b-tetrahydro-1H-cyclopenta[c]quinoline 4-amino-7-phenoxy-2,3,3a,9b-tetrahydro-1H-cyclopenta[c]quinoline 4,7-diamino-2,3,3a,9b-tetrahydro-1H-cyclopenta[c]quinoline 7-acetamido-4-amino-2,3,3a,9b-tetrahydro-1H-cyclopenta[c]quinoline 4-amino-7-(2-phenylethenyl)-2,3,3a,9b-tetrahydro-1H-cyclopenta[c]quinoline 4-amino-7-(2-phenylethinyl)-2,3,3a,9b-tetrahydro-1H-cyclopenta[c]quinoline 7-acetyl-4-amino-2,3,3a,9b-tetrahydro-1H-cyclopenta[c]quinoline 4-amino-2,3,3a,9b-tetrahydro-1H-cyclopenta[c]quinoline-7carboxylic acid methyl ester 4-amino-2,3,3a,9b-tetrahydro-1H-cyclopenta[c]quinoline-7-carboxylic acid-ethyl ester 4-amino-2,3,3a,9b-tetrahydro-1H-cyclopenta[c]quinoline-7-carboxylic acid amide 4-amino-7-cyano-2,3,3a,9b-tetrahydro-1H-cyclopenta[c]quinoline 4-amino-7-trifluoromethyl-2,3,3a,9b-tetrahydro-1H-cyclopenta[c]quinoline 4-amino-7-chloro-2,3,3a,9b-tetrahydro-1H-cyclopenta[c]quinoline 4-amino-7-bromo-2,3,3a,9b-tetrahydro-1H-cyclopenta[c]quinoline 4-amino-7-methylthio-2,3,3a,9b-tetrahydro-1H-cyclopenta[c]quinoline 4-amino-7-(4-methyl-1-piperazinyl)-2,3,3a,9b-tetrahydro-1H-cyclopenta[c]quinoline 4-amino-6-methoxy-2,3,3a,9b-tetrahydro-1H-cyclopenta[c]quinoline 4-amino-8-methoxy-2,3,3a,9b-tetrahydro-1H-cyclopenta[c]quinoline 4-amino-2-thia-2,3,3a,9b-tetrahydro-1H-cyclopenta[c]quinoline 4-amino-2-methyl-2-aza-2,3,3a,9b-tetrahydro-1H-cyclopenta[c]quinoline 4-n-propylamino-2,3,3a,9b-tetrahydro-1H-cyclopenta[c]quinoline 4-amino-6,7-difluoro-2,3,3a,9b-tetrahydro-1H-cyclopenta[c]quinoline 4-amino-8-chloro-6,7-difluoro-2,3,3a,9b-tetrahydro-1H-cyclopenta[c]quinoline

What is claimed is:

1. A compound of Formula 1, a tautomeric form or isomeric form thereof, or a physiologically compatible salt thereof,

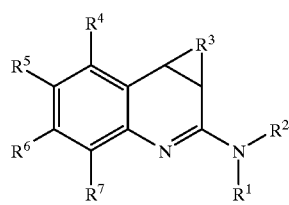

(I)

in which

R$^1$ and R$^2$, independently of one another, mean a) Hydrogen, b) C$_{1-6}$ alkyl, c) OR$^8$, d) NR$^8$R$^9$, e) CN, f) acyl, g) $CO_2R^{10}$, h) $CONR^8R^9$, or i) $CSNR^8R^9$;

$R^3$ is a saturated $C_3$ alkylene in which optionally one $CH_2$ group is replaced by O, S, or NR or a $C_4$–$C_5$ saturated alkylene, which in each case is unsubstituted or substituted by $OR^{11}$, $NR^{12}R^{13}$ or $C_{1-4}$ alkyl, $R^4$, $R^5$, $R^6$ and $R^7$, independently of one another, mean:

a) Hydrogen, b) halogen, c) $S(O)_NR^{16}$, d) $OR^{16}$, e) $COOR^{16}$, f) $COR^{16}$, g) $CONR^{16}R^{17}$, h) $CSNR^{16}R^{17}$, i) $C(NR^{18})NR^{16}R^{17}$, j) $NR^{16}R^{19}$, k) $C_{1-6}$ alkyl, which optionally is substituted with halogen, $OR^{16}$, $SR^{16}$, $COOR^{16}$, phenyl, 5- to 6-membered heteroaryl with 1–4 N, S or O atoms or $C^{3-7}$ cycloalkyl, l) $C_{3-7}$ cycloalkyl, m) $C_{2-6}$ alkenyl, optionally substituted with phenyl or halogen, n) $C_{2-6}$ alkinyl, optionally substituted with phenyl or halogen, o) $C_{6-10}$ aryl, which optionally is substituted with halogen, CN, $C_{1-4}$ alkyl, $SR^{16}$ or $OR^{16}$, p) 5- to 6-membered heteroaryl with 1 to 4 N, O or S atoms, which is annellated with benzene and is optionally substituted with halogen, $NO_2$, cyano, —$OR^{16}$, $SR^{16}$, $C_{1-4}$ alkyl, $CF_3$ or $NR^{16}R^{17}$, q) CN, r) $NO_2$, s) $CF_3$, or t) $OCF_3$;

$R^8$, $R^9$, $R^{10}$, $R^{11}$, $R^{16}$, $R^{18}$, $R^{21}$ and $R^{22}$, independently of one another, mean:

a) Hydrogen, b) $C_{1-6}$ alkyl, or c) $C_{6-10}$ aryl, which optionally is substituted with halogen or $C_{1-4}$ alkyl;

$R^{20}$ means a) $C_{1-6}$ alkyl, or b) $C_{6-10}$ aryl, which optionally is substituted with halogen or $C_{1-4}$ alkyl;

$R^{12}$, $R^{13}$, $R^{14}$ and $R^{19}$, independently of one another, mean:

a) Hydrogen, b) $C_{1-6}$ alkyl, c) $COR^{20}$, d) $CO_2R^{21}$, e) $CONR^{21}R^{22}$, or f) $CSNR^{21}R^{22}$;

$R^{17}$ means a) Hydrogen, b) $C_{1-6}$ alkyl, optionally substituted with halogens, and amino, hydroxy or sulfhydryl groups, or c) $C_{6-10}$ aryl;

n means 0, 1, 2; and $R^{16}$ and $R^{19}$ together with the nitrogen atom optionally form a saturated 5-, 6- or 7-membered ring, which optionally contains another nitrogen, oxygen, or sulfur atom and is optionally substituted with $C_{1-4}$ alkyl or with an optionally halogenated phenyl, benzyl or benzoyl radical.

2. A compound according to claim 1, in which $R^1$ and $R^2$, independently of one another, mean hydrogen, $C_{1-6}$ alkyl or hydroxy.

3. A compound according to calim 1, in which $R^4$, $R^5$, $R^6$ and $R^7$, independently of one another, mean:

a) Hydrogen, b) halogen, c) $SR^{16}$, d) $OR^{16}$, e) $COOR^{16}$, f) $COR^{16}$, g) $CONR^{16}R^{17}$, h) $NR^{16}R^{19}$, i) $C_{1-6}$ alkyl, which optionally is substituted with halogen, $COOR^{16}$ or phenyl, j) $C_{2-6}$ alkenyl, optionally substituted with phenyl or halogen, k) $C_{2-6}$ alkinyl, optionally substituted with phenyl or halogen, l) phenyl, which optionally is substituted with halogen, CN, $C_{1-4}$ alkyl, $SR^{16}$ or $OR^{16}$, m) 5- to 6-membered heteroaryl with 1 to 4 N, O or S atoms, which can be substituted with halogen, $NO_2$, cyano, $C_{1-4}$ alkyl or $CF_3$, n) CN, o) $NO_2$, p) $CF_3$, q) $OCF_3$.

4. A compound according to claim 1, wherein said compound is:

4-Amino-2,3,3a,9b-tetrahydro-1H-cyclopenta[c]quinoline or a physiologically compatible salt thereof;

6-amino-6a,7,8,9,10,10a-hexahydrophenanthridine or a physiologically compatible salt thereof; or 6-amino-2,3,4,5,5a,11b-hexahydro-1H-cyclohepta[c]quinoline or a physiologically compatible salt thereof.

5. A pharmaceutical composition comprising a compound according to claim 1 and a physiologically acceptable vehicle.

6. Process for the production of compounds according to claim 1, comprising the step of reacting a compound of Formula (II) or its salt

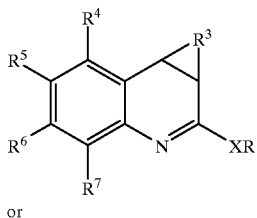

(IIa)

or

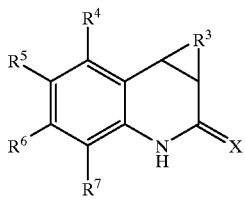

(IIb)

in which $R^3$ to $R^7$ have the above meaning of claim 1, R is methyl or ethyl and X is oxygen or sulfur, with ammonia, primary or secondary amines, hydroxylamine or hydrazine, and optionally seperating the isomers or forming the salts.

7. A method of treating a patient having a disease caused by the action of nitrogen monoxide at pathological concentration, comprising administering to the patient in need thereof a NOS-synthase inhibiting amount of a compound according to claim 1.

8. A compound of Formula 1, a tautomeric form or isomeric form thereof, or a physiologically compatible salt thereof,

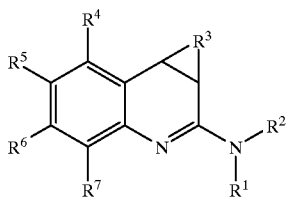

(I)

in which $R^1$ and $R^2$, independently of one another, mean
a) Hydrogen,
b) $C_{1-6}$ alkyl,
c) $OR^8$,
d) $NR^8R^9$,
e) CN,
f) acyl,
g) $CO_2R^{10}$,
h) $CONR^8R^9$, or
i) $CSNR^8R^9$;

$R^3$ is a saturated $C_3$ alkylene in which, optionally one $CH_2$ group is replaced by O, S, or $NR^{14}$ or a $C_4$–$C_5$ saturated alkylene, $R^4$, $R^5$, $R^6$ and $R^7$, independently of one another, mean:
a) Hydrogen,
b) halogen,
c) $S(O)_nR^{16}$,
d) $OR^{16}$,
e) $COOR^{16}$,
f) $CONR^{16}R^{17}$,
g) $CONR^{16}R^{17}$,
h) $CSNR^{16}R^{17}$,
i) $C(NR^{18})NR^{16}R^{17}$,
j) $NR^{16}R^{19}$,
k) $C_{1-6}$alkyl, which optionally is substituted with halogen, $OR^{16}$, $SR^{16}$, $COOR^{16}$, phenyl, 5- to 6-membered heteroaryl with 1–4 N, S or O atoms or $C_{3-7}$ cycloalkyl,
l) $C_{3-7}$ cycloalkyl,
m) $C_{2-6}$ alkenyl, optionally substituted with phenyl or halogen,
n) $C_{2-6}$ alkinyl, optionally substituted with phenyl or halogen,
o) $C_{6-10}$ aryl, which optionally is substituted with halogen, CN, $C_{1-4}$ alkyl, $SR^{16}$ or $OR^{16}$,
p) 5- to 6-membered heteroaryl with 1 to 4 N, O or S atoms, which is annellated with benzene and optionally substituted with halogen, $NO_2$, cyano, —$OR^{16}$, $SR^{16}$, $C_{1-4}$ alkyl, $CF_3$ or $NR^{16}R^{17}$,
q) CN,
r) $NO_2$,
s) $CF_3$, or
t) $OCF_3$;

$R^8$, $R^9$, $R^{10}$, $R^{11}$, $R^{16}$, $R^{18}$, $R^{21}$ and $R^{22}$, independently of one another, mean:
a) Hydrogen,
b) $C_{1-6}$ alkyl, or
c) $C_{6-10}$ aryl, which optionally is substituted with halogen or $C_{1-4}$ alkyl;

$R^{20}$ means
a) $C_{1-6}$ alkyl, or
b) $C_{6-10}$ (aryl, which optionally is substituted with halogen or $C_{1-4}$ alkyl;

$R^{12}$, $R^{13}$, $R^{14}$ and $R^{19}$, independently of one another, mean:
a) Hydrogen,
b) $C_{1-6}$ alkyl,
c) $COR^{20}$,
d) $CO_2R^{21}$,
e) $CONR^{21}R^{22}$, or
f) $CSNR^{21}R^{22}$, $R^{17}$ means
a) Hydrogen,
b) $C_{1-6}$ alkyl, optionally substituted with halogens, and amino, hydroxy or sulfhydryl groups, or
c) $C_{6-10}$ aryl;

n means 0, 1, 2; and $R^{16}$, $R^{19}$ together with the nitrogen atom optionally form a saturated 5-, 6- or 7-membered ring, which optionally contains another nitrogen, oxygen, or sulfur atom and is optionally substituted with $C_{1-4}$ alkyl or with an optionally halogenated phenyl, benzyl or benzoyl radical.

9. A compound according to claim 1, wherein $R^3$ is a saturated $C_3$ alkylene in which one $CH_2$ group is optionally replaced with O or S.

10. A compound according to claim 9, wherein $R^3$ is —$CH_2$—O—$CH_2$—, —$CH_2$—S—$CH_2$—, —$(CH_2)_3$—, —$(CH_2)_4$— or —$(CH_2)_5$—.

11. A compound according to claim 1, wherein acyl is derived from a straight-chain or branched aliphatic $C_{1-6}$ carboxylic acid, benzylsulfonic acid which is optionally substituted with halogen or $C_{1-4}$ alkyl, or a $C_{1-4}$ alkanesulfonic acid.

12. A compound according to claim 1, wherein $R^{12}$, $R^{13}$, $R^{14}$, $R^{17}$ and $R^{19}$ are each independently hydrogen or $C_{1-6}$ alkyl.

13. A compound according to claim 1, wherein one or two of $R^4$, $R^5$, $R^6$ or $R^7$ are other than hydrogen.

14. A method according to claim 7, wherein said compound is administered in a daily dose of 1–2000 mg.

15. A method according to claim 7, wherein said compound is administered in a daily dose of 20–500 mg.

16. A compound according to claim 1, wherein at least one of $R^4$, $R^5$, $R^6$ and $R^7$ is a hetaroaryl or $C_{1-6}$ alkyl substituted by a heteroaryl, wherein the heteroaryl is a radical of imidazole, indole, isoxazole, isothiazole, furan, oxadiazole, oxazole, pyrazine, pyridazine, pyrimidine, pyridine, pyrazole, pyrrole, tetrazole, thiazole, triazole, thiophene, thiadiazole, benzimidazole, benzofuran, benzoxazole, isoquinoline or quinoline.

17. A compound according to claim 1, wherein at least one of $R^4$, $R^5$, $R^6$ and $R^7$ is a heteroaryl or a $C_{1-6}$ alkyl substituted by a heteroaryl, wherein said heteroaryl is furanyl or thienyl.

18. A compound according to claim 1, wherein $NR^{16}R^{19}$ is a radical of piperidine, pyrrolidine, morpholine, thiomorpholine, hexahydroazepine or piperazine, which in each case is unsubstituted or substituted in 1 to 3 places by $C_{1-4}$ alkyl, phenyl, phenyl substituted with halogen, benzyl, benzyl substituted with halogen, benzoyl, or benzoyl substituted with halogen.

19. A compound according to claim 1, wherein $R^3$ is —(CH$_2$)$_5$—.

20. A compound according to claim 1, wherein said compound is:

4-Amino-2,3,3a,9b-tetrahydro-1H-cyclopenta[c]quinoline, or a physiologically compatible salt thereof;

6-Amino-2,3,4,5,5a,11b-hexahydro-1H-cyclohepta[c]quinoline, or a physiologically compatible salt thereof;

4-Amino-7-nitro-2,3,3a,9b-tetrahydro-1H-cyclopenta[c]quinoline, or a physiologically compatible salt thereof;

4-Amino-8-methyl-7-nitro-2,3,3a,9b-tetrahydro-1H-cyclopenta[c]quinoline, or a physiologically compatible salt thereof;

4-Amino-8-nitro-2,3,3a,9b-tetrahydro-1H-cyclopenta[c]quinoline, or a physiologically compatible salt thereof;

4-Amino-2-oxa-2,3,3a-9b-hexahydro-1H-cyclopenta[c]quinoline, or a physiologically compatible salt thereof;

4-Amino-7-methoxy-2,3,3a,9b-tetrahydro-1H-cyclopenta[c]quinoline, or a physiologically compatible salt thereof;

4-Amino-8-methoxy-2,3,3a,9b-tetrahydro-1H-cyclopenta[c]quinoline, or a physiologically compatible salt thereof;

4-Amino-7-methyl-2,3,3a,9b-tetrahydro-1H-cyclopenta[c]quinoline, or a physiologically compatible salt thereof;

4-Amino-8-methyl-2,3,3a,9b-tetrahydro-1H-cyclopenta[c]quinoline, or a physiologically compatible salt thereof;

4-Amino-8-chloro-2,3,3a,9b-tetrahydro-1H-cyclopenta[c]quinoline, or a physiologically compatible salt thereof;

4-Amino-6,8-dichloro-2,3,3a,9b-tetrahydro-1H-cyclopenta[c]quinoline, or a physiologically compatible salt thereof;

4-Amino-8-bromo-2,3,3a,9b-tetrahydro-1H-cyclopenta[c]quinoline, or a physiologically compatible salt thereof;

4-Amino-8-(trifluoromethyl)-2,3,3a,9b-tetrahydro-1H-cyclopenta[c]quinoline, or a physiologically compatible salt thereof;

4-Amino-8-cyano-2,3,3a,9b-tetrahydro-1H-cyclopenta[c]quinoline, or a physiologically compatible salt thereof;

4-Amino-8-fluoro-2,3,3a,9b-tetrahydro-1H-cyclopenta[c]quinoline, or a physiologically compatible salt thereof;

4-Amino-7-fluoro-2,3,3a,9b-tetrahydro-1H-cyclopenta[c]quinoline, or a physiologically compatible salt thereof;

4-Amino-6-fluoro-2,3,3a,9b-tetrahydro-1H-cyclopenta[c]quinoline, or a physiologically compatible salt thereof;

4-Amino-7-(2-furanyl)-2,3,3a,9b-tetrahydro-1H-cyclopenta[c]quinoline, or a physiologically compatible salt thereof;

4-Amino-7-(4-morpholinyl)-2,3,3a,9b-tetrahydro-1H-cyclopenta[c]quinoline, or a physiologically compatible salt thereof;

4-Amino-7-(methoxycarbonylethyl)-2,3,3a,9b-tetrahydro-1H-cyclopentatc]quinoline, or a physiologically compatible salt thereof;

4-Methylamino-2,3,3a,9b-tetrahydro-1H-cyclopenta[c]quinoline, or a physiologically compatible salt thereof;

4-Ethylamino-2,3,3a,9b-tetrahydro-1H-cyclopenta[c]quinoline, or a physiologically compatible salt thereof;

4-Amino-7-hydroxy-2,3,3a,9b-tetrahydro-1H-cyclopenta[c]quinoline, or a physiologically compatible salt thereof;

4-amino-7-phenoxy-2,3,3a,9b-tetrahydro-1H-cyclopenta[c]quinol ine, or a physiologically compatible salt thereof;

4,7-diamino-2,3,3a,9b-tetrahydro-1H-cyclopenta[c]quinoline, or a physiologically compatible salt thereof;

7-acetamido-4-amino-2,3,3a,9b-tetrahydro-1H-cyclopenta[c]quinoline, or a physiologically compatible salt thereof;

4-amino-7-(2-phenylethenyl)-2,3,3a,9b-tetrahydro-1H-cyclopenta[c]quinoline, or a physiologically compatible salt thereof;

4-amino-7(2-phenylethinyl)2,3,3a,9b-tetrahydro-1H-cyclopenta[c]quinoline, or a physiologically compatible salt thereof;

7-acetyl-4-amino-2,3,3a,9b-tetrahydro-1H-cyclopenta[c]quinoline, or a physiologically compatible salt thereof;

4-amino-2,3,3a,9b-tetrahydro-1H-cyclopenta[c]quinoline-7-carboxylic acid methyl ester, or a physiologically compatible salt thereof;

4-amino-2,3,3a,9b-tetrahydro-1H-cyclopenta[c]quinoline-7-carboxylic acid-ethyl ester, or a physiologically compatible salt thereof;

4-amino-2,3,3a,9b-tetrahydro-1H-cyclopenta[c]quinoline-7-carboxylic acid amide, or a physiologically compatible salt thereof;

4-amino-7-cyano-2,3,3a,9b-tetrahydro-1H-cyclopenta[c]quinoline, or a physiologically compatible salt thereof;

4-amino-7-trifluoromethyl-2,3,3a,9b-tetrahydro-1H-cyclopenta[c]quinoline, or a physiologically compatible salt thereof;

4-amino-7-chloro-2,3,3a,9b-tetrahydro-1H-cyclopenta[c]quinoline, or a physiologically compatible salt thereof;

4-amino-7-bromo-2,3,3a,9b-tetrahydro-1H-cyclopenta[c]quinoline, or a physiologically compatible salt thereof;

4-amino-7-methylthio-2,3,3a,9b-tetrahydro-1H-cyclopenta[c]quinoline, or a physiologically compatible salt thereof;

4-amino-7-(4-methyl-1-piperazinyl)2,3,3a,9b-tetrahydro-1H-cyclopenta[c]quinoline, or a physiologically compatible salt thereof;

4-amino-6-methoxy-2,3,3a,9b-tetrahydro-1H-cyclopenta[c]quinoline, or a physiologically compatible salt thereof;

4-amino-8-methoxy-2,3,3a,9b-tetrahydro-1H-cyclopenta[c]quinoline, or a physiologically compatible salt thereof;

4-amino-2-thia-2,3,3a,9b-tetrahydro-1H-cyclopenta[c]quinoline, or a physiologically compatible salt thereof;

4-amino-2-methyl-2-aza-2,3,3a,9b-tetrahydro-1H-cyclopenta[c]quinoline, or a physiologically compatible salt thereof;

4-n-propylamino-2,3,3a,9b-tetrahydro-1H-cyclopenta[c]quinoline, or a physiologically compatible salt thereof;

4-amino-6,7-difluoro-2,3,3a,9b-tetrahydro-1H-cyclopenta[c]quinoline, or a physiologically compatible salt thereof; or 4-amino-8-chloro-6,7-difluoro-2,3,3a,9b-tetrahydro-1H-cyclopenta[c]quinoline, or a physiologically compatible salt.

21. A compound according to claim 1, wherein $R^3$ is a saturated $C_3$–$C_5$ alkylene.

* * * * *